(12) United States Patent
Nishino et al.

(10) Patent No.: US 8,318,792 B2
(45) Date of Patent: Nov. 27, 2012

(54) THERAPEUTIC AGENT FOR AMYOTROPHIC LATERAL SCLEROSIS

(75) Inventors: Takeshi Nishino, Tokyo (JP); Yasuko Abe, Tokyo (JP); Shinsuke Kato, Yonago (JP)

(73) Assignees: Nippon Medical School Foundation, Tokyo (JP); National University Corporation Tottori University, Tottori-shi (JP)

( * ) Notice: Subject to any disclaimer, the term of this patent is extended or adjusted under 35 U.S.C. 154(b) by 738 days.

(21) Appl. No.: 12/374,187

(22) PCT Filed: Jul. 13, 2007

(86) PCT No.: PCT/JP2007/000765
§ 371 (c)(1),
(2), (4) Date: Mar. 24, 2009

(87) PCT Pub. No.: WO2008/010315
PCT Pub. Date: Jan. 24, 2008

(65) Prior Publication Data
US 2010/0010054 A1    Jan. 14, 2010

(30) Foreign Application Priority Data

Jul. 19, 2006  (JP) ................................. 2006-196343

(51) Int. Cl.
*A61K 31/415*     (2006.01)
*A61K 31/426*     (2006.01)
*A61K 31/4439*    (2006.01)

(52) U.S. Cl. ......... 514/406; 514/365; 514/340; 514/333
(58) Field of Classification Search ........................ None
See application file for complete search history.

(56) References Cited

U.S. PATENT DOCUMENTS

| | | | |
|---|---|---|---|
| 5,614,520 | A | 3/1997 | Kondo et al. |
| 6,015,829 | A | 1/2000 | Ishibuchi et al. |
| 2005/0004175 | A1 | 1/2005 | Nakamura et al. |

FOREIGN PATENT DOCUMENTS

| | | |
|---|---|---|
| CA | 2 117 466 | 9/1993 |
| EP | 0 513 379 A1 | 11/1992 |
| EP | 0 779 074 A1 | 6/1997 |
| EP | 1 471 065 A1 | 10/2004 |
| EP | 1 609 479 A1 | 12/2005 |
| JP | 7-504655 | 5/1995 |
| JP | 2002 105067 | 4/2002 |
| WO | 92 09279 | 6/1992 |
| WO | WO 93/17683 | 9/1993 |
| WO | 98 18765 | 5/1998 |
| WO | 03 064410 | 8/2003 |

OTHER PUBLICATIONS

Nishino, T., The Journal of Biochemistry, (1993), 116(1), pp. 1-6 (Abstract).*
The Merck Manual, 17th edition (1999), pp. 1486-1487.*
J.M. Charcot et al., "Deux Cas D'Atrophie Musculaire Progressive: Avec Lesions De La Substance Grise et Des Faisceaux Antero-Lateraux De La Moelle Epiniere", Archives of Physiology, 1869; 2, pp. 744-760.
Shinsuke Kato, et al., "Neurodegeneration: The Molecular Pathology of Dementia and Movement Disorders; Amyotrophic Lateral Sclerosis", ISN Neuropathology Press, 2003, pp. 350-368.
Arthur J. Hudson, "Amyotrophic Lateral Sclerosis and its Association With Dementia, Parkinsonism and Other Neurological Disorders: A Review", Brain (1981), vol. 104, pp. 217-247.
Tony Juneja, et al., "Prognosis in Familial Amyotrophic Lateral Sclerosis: Progression and survival in patients with Glu100gly and Ala4val Mutations in Cu,Zn Superoxide dismutase", The American Academy of Neurology, vol. 48, Jan. 1997, pp. 55-57.
Han-Xiang Deng, et al., "Amyotrophic Lateral Sclerosis and Structural Defects in Cu,Zn Superoxide Dismutase", Science, vol. 261, Aug. 1993, pp. 1047-1051.
Daniel R. Rosen, et al., "Mutations in Cu/Zn Superoxide Dismutase Gene are Associated With Familial Amyotrophic Lateral Sclerosis", Nature, vol. 362, Mar. 1993, pp. 59-62.
Mark E. Gurney, et al., "Motor Neuron Degeneration in Mice That Express a Human Cu,Zn Superoxide Dismutase Mutation", Science, vol. 264, Jun. 1994, pp. 1772-1775.
Dairin Kieran, et al., "Treatment With Arimoclomol, a Coinducer of Heat Shock Proteins, Delays Disease Progression in ALS Mice", Nature Medicine, vol. 10, No. 4, Apr. 2004. pp. 402-405.
Terro, F. et al., "Antioxidant drug block in vitro the neurotoxicity of CSF from patients with amyotrophic lateral sclerosis", Neuroreport, vol. 7, pp. 1970-1972, (1996).
Berger, R. et al., "Analysis of aldehyde oxidase and xanthine dehydrogenase/oxidase as possible candidate genes for autosomal recessive familial amyotrophic lateral sclerosis", Somatic Cell and Molecular Genetics, vol. 21, No. 2, pp. 121-131, (1995).

* cited by examiner

*Primary Examiner* — Phyllis G. Spivack
(74) *Attorney, Agent, or Firm* — Oblon, Spivak, McClelland, Maier & Neustadt, L.L.P.

(57) ABSTRACT

A method for treating amyotrophic lateral sclerosis is disclosed wherein a compound having xanthine dehydrogenase inhibiting activity is administered.

13 Claims, 16 Drawing Sheets

Significance between experimental group administered with placebo and treatment experimental group administered with compound (a) from before onset; $P < 0.0001$ Significance between experimental group administered with placebo and treatment experimental group administered with compound (a) before onset; $P < 0.0001$ Fig, 8
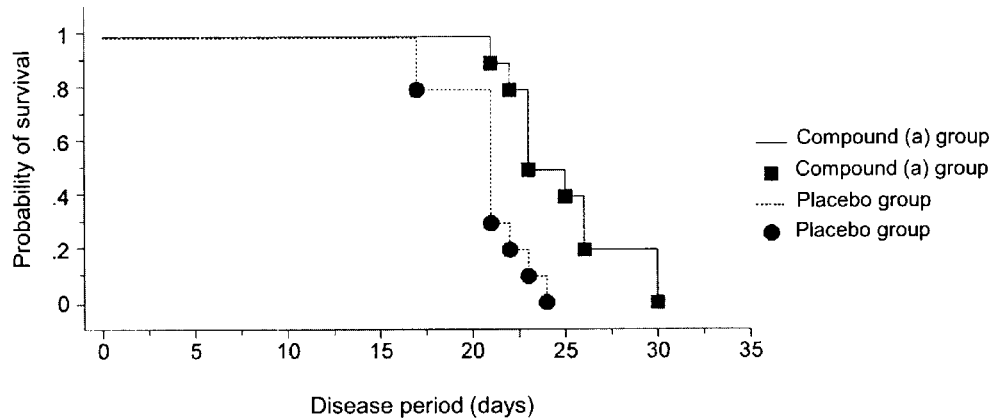
Significance between experimental group administered with placebo and treatment experimental group administered with compound (a) before onset; P < 0.002
Fig. 9
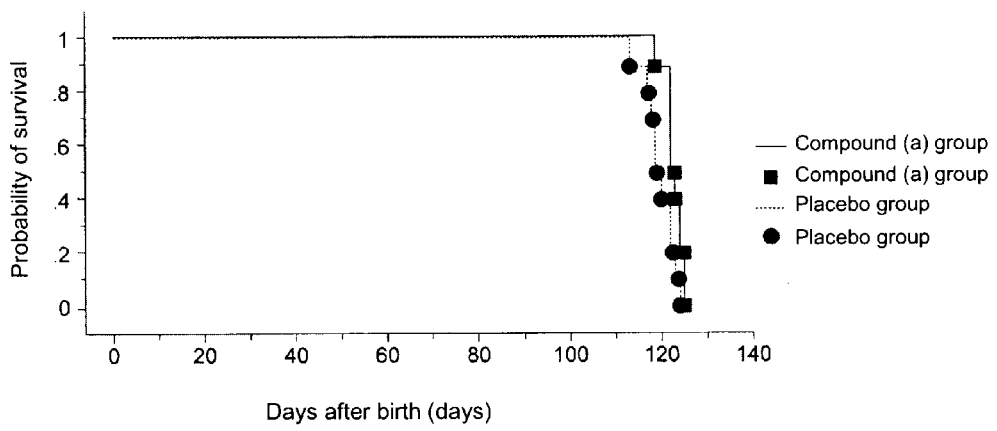
Significance between experimental group administered with placebo and treatment experimental group administered with compound (a) after onset; P = 0.024

Significance between experimental group administered with placebo and treatment experimental group administered with compound (a) after onset; P = 0.003

Significance between experimental group administered with placebo and treatment experimental group administered with compound (b) before onset; P < 0.0001

Significance between experimental group administered with placebo and treatment experimental group administered with compound (b) before onset; $P < 0.0001$ Significance between experimental group administered with placebo and treatment experimental group administered with compound (b) before onset; $P < 0.005$ Significance between experimental group administered with placebo and treatment experimental group administered with compound (c) before onset; P < 0.0001

Significance between experimental group administered with placebo and treatment experimental group administered with compound (c) before onset; P < 0.0001

Significance between experimental group administered with placebo and treatment experimental group administered with compound (c) before onset; P < 0.0005

Significance between experimental group administered with placebo and treatment experimental group administered with compound (c) after onset; P = 0.0065

Significance between experimental group administered with placebo and treatment experimental group administered with compound (c) after onset; P = 0.015

Significance between experimental group administered with placebo and treatment experimental group administered with allopurinol before onset; P = 0.1162

Significance between experimental group administered with placebo and treatment experimental group administered with allopurinol before onset; P = 0.1310

Significance between experimental group administered with placebo and treatment experimental group administered with allopurinol before onset; P = 0.6003

THERAPEUTIC AGENT FOR AMYOTROPHIC LATERAL SCLEROSIS

CROSS-REFERENCE TO RELATED APPLICATIONS

This application is a 371 of PCT/JP07/00765 filed Jul. 13, 2007 and claims the benefit of JP 2006-196343 filed Jul. 19, 2006.

TECHNICAL FIELD

The present invention relates to a therapeutic agent for amyotrophic lateral sclerosis.

BACKGROUND ART

Amyotrophic lateral sclerosis (hereinafter, ALS) is a representative fatal neurodegenerative disease for which the establishment of effective therapy is strongly desired. In Japan, ALS has been designated as a specific intractable disease by the Ministry of Health, Labour and Welfare. The prevalence rate of ALS is regarded to be about 3 to 5 persons in a population of 100,000, and currently, it is believed that there are about 4,000 to 5,000 patients in Japan. In addition, ALS occurs after the middle age, which is the prime of one's life. Therefore, development of a novel therapy for ALS is extremely important.

From a historical standpoint, ALS is one disease entity described by Charcot and Joffroy in 1869 (Non-Patent Document 1). It is a progressive disease of unknown cause, in which both of the upper motor neuron and the lower motor neuron are generally impaired, and has been regarded as a motor neuron disease leading to death from paralysis of respiratory muscles (Non-Patent Document 2). Although it has been about 130 years since ALS was firstly reported, no effective therapy for the disease has been established. The effects of drugs based on neurotrophic factors, neuroprotective effects, caspase inhibition, copper chelating action, glutamate inhibitory action, and antioxidants have been investigated to discover the therapeutic agents for ALS. However, the only product currently marketed as a therapeutic agent for ALS is riluzole, which has glutamate inhibitory action as an agonist of glutamate receptors (Patent Document 1).

Antioxidants, namely, vitamin E which is a free radical scavenger, and allopurinol which is a xanthine oxidase inhibitor, are known to counteract the neurotoxin in cerebrospinal fluid from ALS patients in vitro (Non-Patent Document 3).

About 5 to 10% of ALS are familial amyotrophic lateral sclerosis (hereinafter, FALS) (Non-Patent Documents 4 and 5). As an etiological clue for ALS, in 1993, it was reported that about 20% of the FALS have copper/zinc superoxide dismutase (SOD1) gene mutation (Non-Patent Documents 2, 6 and 7). Based on this report, the transgenic mouse which expresses human mutated SOD1 gene at a high level has been developed (Non-Patent document 8). This transgenic mouse exhibits symptoms of motor paralysis due to motor neuron disorder in the same symptom as in human ALS, and the mouse eventually shows quadriplegia and a moribund state, and then exhibits respiratory muscle paralysis and dies. In addition, the mouse also exhibits histopathological findings of motor neuron disorder which are histopathologically identical to that of human. Therefore, this transgenic mouse is useful as an animal model for human ALS. Recently, it has been reported that arimoclomol, which is a hydroxylamine derivative with HSP (heat shock protein)-inducing action, leads to prolongation of life in the transgenic mouse, and thus being useful against ALS (Non-Patent Document 9).

[Patent Document 1] Japanese Patent No. 2713384
[Non-Patent Document 1] Charcot J M & Joffroy A. Arch Physiol (Paris) 1869; 2:744-760
[Non-Patent Document 2] Kato, et al. Neurodegeneration: The Molecular Pathology of Dementia and Movement Disorders. ISN Neuropath Press, 2003: pp. 350-368
[Non-Patent Document 3] Neuroreport, Vol. 7, No. 12, p. 1970-1972, 12, Aug., 1996
[Non-Patent Document 4] Hudson A J. Brain 1981; 104: 217-247
[Non-Patent Document 5] Juneja T, et al. Neurology 1997; 48:55-57
[Non-Patent Document 6] Deng H X, et al. Science 1993; 261:1047-1051
[Non-Patent Document 7] Rosen D R, et al. Nature 1993; 362:59-62
[Non-Patent Document 8] Gurney M E, et al. Science 1994; 264:1772-1775
[Non-Patent Document 9] Nature Medicine, 10:402-405, 2004

DISCLOSURE OF THE INVENTION

Problems to be Solved by the Invention

However, the therapeutic effect of riluzole on ALS is not satisfactory, and also, antioxidants such as vitamin E and allopurinol are not effective in the treatment of ALS. The therapeutic effect of arimoclomol is also not satisfactory in the effectiveness.

Therefore, further development of a new therapeutic agent for ALS is desired.

Means for Solving the Problems

Under such circumstances, the inventors of the present invention have conducted an investigation on the ALS treating effect of various drugs using a transgenic mouse overexpressing human mutated SOD1, and unexpectedly found that a compound having xanthine dehydrogenase inhibitory action and not acting as a substrate for the purine salvage pathway, exhibits markedly excellent ALS treating effect in comparison to allopurinol, thereby completing the present invention.

Accordingly, the present invention provides a therapeutic agent for ALS, comprising a compound having xanthine dehydrogenase inhibitory action and not acting as a substrate for the purine salvage pathway.

Furthermore, the present invention provides a use of a compound having xanthine dehydrogenase inhibitory action and not acting as a substrate for the purine salvage pathway, for the manufacture of a therapeutic agent for ALS.

Also, the present invention provides a method for preventing or treating ALS, which comprises administering an effective amount of a compound having xanthine dehydrogenase inhibitory action and not acting as a substrate for the purine salvage pathway.

Effects of the Invention

According to the present invention, prevention of the onset and delay of the progress of ALS, and prolongation of life can be accomplished by administering the compound having xanthine dehydrogenase inhibitory action. Therefore, ALS can be treated in accordance with the present invention.

The ALS treating effect of the compound of the present invention is markedly potent as compared to allopurinol, which is likewise a xanthine dehydrogenase inhibitor. Furthermore, since the background mechanism of ALS treating effect of arimoclomol is different from that of the compound of the present invention, they are administered in accordance with different regimens. According to Non-Patent Document 9, arimoclomol is effective under intraperitoneal administration in an amount of 10 mg/kg, while the compound of the present invention is effective even under oral administration in amount of 5 mg/kg. Therefore, the compound of the present invention has an extremely potent ALS treating effect, even in comparison to arimoclomol.

BRIEF DESCRIPTION OF THE DRAWINGS

FIG. 8 is a diagram showing the results of a log-rank test of the Kaplan-Meier's method with regard to the disease period, for the experimental group administered with placebo and the treatment experimental group administered with compound (a) before onset. The vertical axis represents the probability of survival, and the horizontal axis represents disease period.

FIG. 9 is a diagram showing the results of a log-rank test of the Kaplan-Meier's method with regard to the survival period, for the experimental group administered with placebo and the treatment experimental group administered with compound (a) after onset. The vertical axis represents the probability of survival, and the horizontal axis represents days after birth.

DETAILED DESCRIPTION OF THE INVENTION

Figure 1:
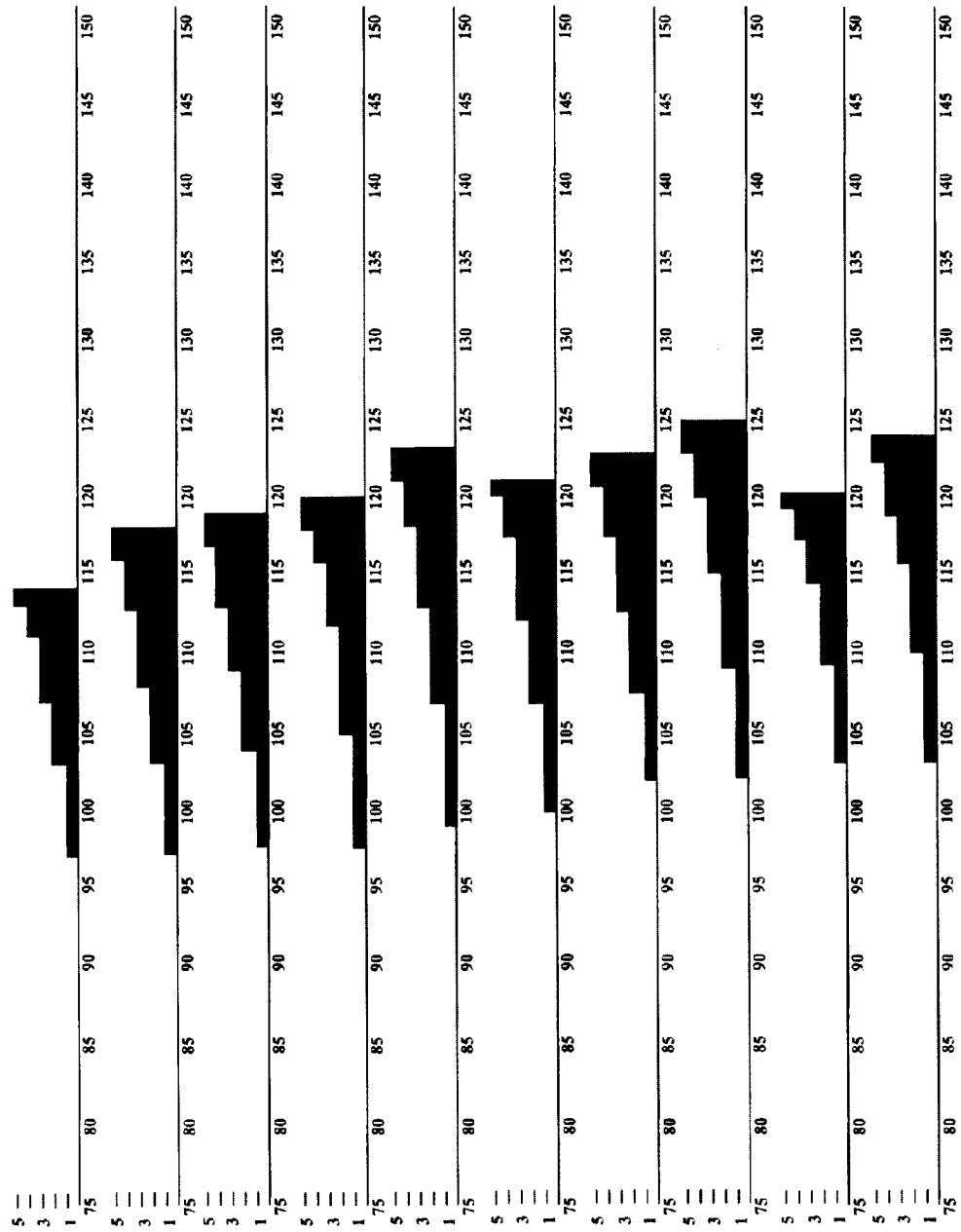
FIG. 1 is a diagram showing a clinical symptomatological evaluation of the respective G1H-G93A transgenic mice in an experimental group administered with placebo. The vertical axis represents the degree of clinical symptomatological stage, and the horizontal axis represents days after birth.

The compound having xanthine dehydrogenase inhibitory action and not acting as a substrate for the purine salvage pathway, which is an active ingredient of the therapeutic agent for ALS of the present invention, is not defined by the chemical structure thereof as long as the compound has the actions described above. Therefore, conventionally existing compounds can be used as the therapeutic agent of ALS of the present invention.

For example, the compound contained in the therapeutic agent of the present invention includes xanthine dehydrogenase inhibitors having a two rings structure having an aromatic ring and an aromatic heterocyclic ring, such as a phenyl-imidazole structure, a phenyl-thiazole structure, a phenyl-triazole structure or a pyridyl-triazole structure, and the like. According to the present invention, the compound more preferred as the therapeutic agent for ALS includes a compound represented by the following formula (1), (2) or (3), and a salt thereof.

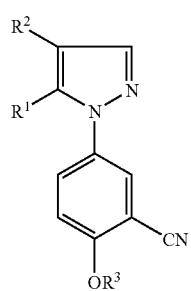

(1)

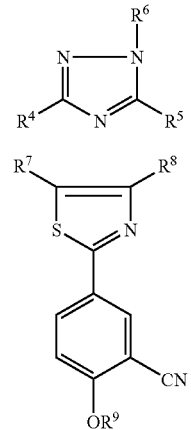

(2)

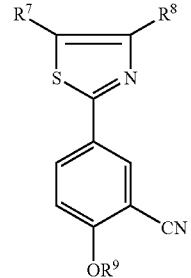

(3)

wherein $R^1$ represents a hydrogen atom, a halogen atom or an amino group;

$R^2$ represents a carboxyl group or a $C_{1-4}$ alkoxycarbonyl group;

$R^3$ represents a $C_{4-6}$ alkyl group, a $C_{3-6}$ cycloalkyl group or a $C_{3-6}$ cycloalkyl-$C_{1-4}$ alkyl group, all of which may be substituted with one to two substituents selected from halogen, hydroxyl, $C_{1-4}$ alkoxy, carboxy, $C_{1-4}$ alkoxycarbonyl and acyloxy;

$R^4$ represents a pyridyl group which may be substituted with one to two substituents selected from halogen, cyano and phenyl; or a phenyl group which may be substituted with one to two substituents selected from cyano, nitro, $C_{1-4}$ alkoxy, N—$C_{1-4}$ alkylpiperazino, $C_{1-4}$ alkylthio, phenylthio and $C_{1-4}$ alkylamino;

$R^5$ represents a pyridyl group which may be substituted with a substituent selected from cyano, $C_{1-4}$ alkyl, halogen, $C_{1-4}$ alkoxy and $C_{1-4}$ alkylthio;

$R^6$ represents a hydrogen atom, or a pivaloyloxy-$C_{1-4}$ alkyl group;

$R^7$ represents a carboxyl group, a $C_{1-6}$ alkoxycarbonyl group, a carbamoyl group, or a mono- or di-$C_{1-6}$ alkylaminocarbonyl group;

$R^8$ represents a hydrogen atom, a $C_{1-6}$ alkyl group or a phenyl group; and $R^9$ represents a hydrogen atom or a $C_{1-10}$ alkyl group.

These compounds have a common two rings structure having an aromatic rings and an aromatic heterocyclic ring, as described above.

These compounds represented by formulas (1), (2) and (3) are described in Japanese Patent No. 3220987, Japanese Patent No. 3600832, JP-A No. 2005-41802, JP-A No. 6-293746, JP-A No. 2002-105067, and the like, and are known to have excellent xanthine dehydrogenase inhibitory action. However, it has never been known that these compounds have an ALS treating action.

In the formula (1), the halogen atom represented by $R^1$ includes a fluorine atom, a chlorine atom, a bromine atom, an iodine atom, and the like. As for $R^1$, a hydrogen atom is more preferred.

The $C_{1-4}$ alkoxycarbonyl group represented by $R^2$ includes an ethoxycarbonyl group, a propoxycabronyl group, and the like. As for $R^2$, a carboxyl group is more preferred.

The $C_{4-6}$ alkyl group represented by $R^3$ includes a straight-chained and branched $C_{4-6}$ alkyl group, and examples thereof include an n-butyl group, an isobutyl group, a tert-butyl group, an n-pentyl group, a neopentyl group (2,2-dimethylpropyl group), an n-hexyl group, and the like. Among these, a neopentyl group is more preferred. The $C_{3-6}$ cycloalkyl group represented by $R^3$ includes a cyclopropyl group, a cyclopentyl group, a cyclohexyl group, and the like. Furthermore, the $C_{3-6}$ cycloalkyl-$C_{1-4}$ alkyl group includes a cyclopropylmethyl group, a cyclopentylmethyl group, a cyclohexylmethyl group, a cyclopentylethyl group, a cycloxylethyl group, and the like. As for $R^3$, a $C_{4-6}$ alkyl group is more preferred, a branched $C_{4-6}$ alkyl group is still more preferred, and a neopentyl group is even still more preferred.

The $C_{4-6}$ alkyl group, $C_{3-6}$ cycloalkyl group or $C_{3-6}$ cycloalkyl-$C_{1-4}$ alkyl group represented by $R^3$ may be substituted with one to two substituents selected from halogen, hydroxyl, $C_{1-4}$ alkoxy, carboxy, $C_{1-4}$ alkoxycarbonyl and acyloxy. The halogen includes fluorine, chlorine, and bromine. The $C_{1-4}$ alkoxy includes methoxy, ethoxy, and the like. The $C_{1-4}$ alkoxycarbonyl includes methoxycarbonyl, ethoxycarbonyl, and the like. The acyloxy includes acetoxy, propionyloxy, and the like.

Among the compounds of formula (1), a more preferred compound is a compound in which $R^1$ is a hydrogen atom, $R^2$ is a carboxyl group, and $R^3$ is a $C_{4-6}$ alkyl group. Among the compounds of formula (1), the most preferred compound is a compound in which $R^1$ is a hydrogen atom, $R^2$ is a carboxyl group, and $R^3$ is a neopentyl group (2,2-dimethylpropyl) (1-(3-cyano-4-(2,2-dimethylpropoxy)phenyl)-1H-pyrazole-4-carboxylic acid).

In the formula (2), the pyridyl group represented by $R^4$ may be substituted with one or two substituents selected from halogen, cyano and phenyl. The halogen atom includes a fluorine atom, a chlorine atom, a bromine atom, and the like.

The phenyl group represented by $R^4$ may be substituted with one to two substituents selected from cyano, nitro, $C_{1-4}$ alkoxy, N—$C_{1-4}$ alkylpiperazino, $C_{1-4}$ alkylthio, phenylthio and $C_{1-4}$ alkylamino. The $C_{1-4}$ alkoxy includes methoxy, ethoxy, and the like. The N—$C_{1-4}$ alkylpiperazino includes N-methylpiperazino, N-ethylpiperazino, and the like. The $C_{1-4}$ alkylthio includes methylthio, ethylthio, and the like. The $C_{1-4}$ alkylamino includes methylamino, ethylamino, isopropylamino, and the like.

Among $R^4$, a cyanopyridyl group is preferred, and a 2-cyanopyridin-4-yl group is more preferred.

The pyridyl group represented by $R^5$ may be substituted with one or two substituents selected from a cyano group, a halogen atom, a $C_{1-6}$ alkoxy group and a $C_{1-6}$ alkylthio group. The examples of the halogen atom, $C_{1-6}$ alkoxy group and $C_{1-6}$ alkylthio group include the same groups as those in the case of $R^4$. As for $R^5$, a pyridyl group is preferred, and a pyridyn-4-yl group is more preferred.

The pivaloyloxy-$C_{1-4}$ alkyl group represented by $R^6$ includes a pivaloyloxymethyl group, a pivaloyloxyethyl group, and the like. As for $R^6$, a hydrogen atom is preferred.

Among the compounds of formula (2), a more preferred compound is a compound in which $R^4$ is a cyanopyridyl group, $R^5$ is a pyridyl group, and $R^6$ is a hydrogen atom. Among the compounds of formula (2), the most preferred compound is a compound in which $R^4$ is a 2-cyanopyridin-4-yl group, $R^5$ is a pyridin-4-yl group, and $R^6$ is a hydrogen atom (4-(5-pyridin-4-yl-1H-[1,2,4]triazol-3-yl)pyridine-2-carbonitrile).

In the formula (3), the $C_{1-6}$ alkoxycarbonyl group represented by $R^7$ includes a methoxycarbonyl group, an ethoxycarbonyl group, an isopropyloxycarbonyl group, a butoxycarbonyl group, and the like. The mono- or di-$C_{1-6}$ alkylaminocarbonyl group includes a methylaminocarbonyl group, an ethylaminocarbonyl group, a dimethylaminocarbonyl group, a diethylaminocarbonyl group, and the like.

Among $R^7$, a carboxyl group or a $C_{1-6}$ alkoxycarbonyl group is more preferred, and a carboxyl group is still more preferred.

The $C_{1-6}$ alkyl group represented by $R^8$ includes a methyl group, an ethyl group, an isopropyl group, a butyl group, a pentyl group, and the like. As for $R^8$, a $C_{1-6}$ alkyl group is preferred, and a methyl group is still more preferred.

The $C_{1-6}$ alkyl group of $R^9$ includes a methyl group, an ethyl group, an isopropyl group, an n-butyl group, an isobutyl group (2-methylpropyl group), a t-butyl group, a pentyl group, a neopentyl group, a hexyl group, an octyl group, and the like. As for $R^9$, a $C_{1-8}$ alkyl group is preferred, a $C_{2-6}$ alkyl group is more preferred, and an isobutyl group (2-methylpropyl group) is still more preferred.

Among the compounds of formula (3), a compound in which $R^7$ is a carboxyl group, $R^8$ is a methyl group, $R^9$ is an isobutyl group (2-[3-cyano-4-(2-methylpropoxy)phenyl]-4-methyl-5-thiazolecarboxylic acid) is particularly preferred.

The salt of the compound represented by formula (1), (2) or (3) includes pharmaceutically-acceptable salts. Examples of the salt include a salt with a metal (sodium, potassium, calcium, or the like) or an organic acid base (diethanolamine, trimethylamine) formed at carboxyl group therein, and an acid addition salt formed at amino group therein, for example a mineral acid salt such as hydrochloride or sulfate and an organic acid salt such as acetate or citrate. The compounds of formulas (1), (2) and (3) include solvates such as hydrate. These compounds also include optical isomers.

The compounds having xanthine dehydrogenase inhibitory action and not acting as a substrate for the purine salvage pathway, specifically the compounds of formulas (1), (2) and (3), have an excellent action of preventing the onset of ALS, an excellent action of delaying the progress of ALS symptoms, and an excellent action of life prolonging against the death caused by ALS, and are useful as therapeutic agents for ALS, as will be shown hereinbelow in Examples. Furthermore, the actions are markedly potent as compared to allopurinol which has xanthine dehydrogenase inhibitory action and acting as a substrate for the purine salvage pathway. In addition, the compounds of formulas (2) and (3) have already been developed as uric acid generation inhibitors, and known to be highly safe. ALS is sometimes diagnosed through the initial symptoms such as sudden dropping of objects in hand, stumbling, and slurred speech. The basic symptoms of ALS include the symptoms of muscular fasciculation, the symptoms of muscular atrophy and muscle weakness, the symptoms of bulbar palsy, and the symptoms of pyramidal tract. The symptoms of muscular fasciculation are recognized in the form of muscular fibrillation. The symptoms of muscular atrophy and muscle weakness start, in many cases, from muscular atrophy and muscle weakness in the distal parts of the upper limbs and/or lower limbs, and eventually come to disorder in the muscles of the proximal parts of the extremities. The early phase symptoms are lowered grip (dropping the objects in hand, or the like) and difficulties in elevating the sole of the foot (the ankle cannot be lifted, or the like), but eventually difficulties in the elevation of the upper limbs or walking disorder (stumbling, tumbling, or the like) are brought about. Thus, movements in the daily life become difficult or impossible, and a bedridden state is attained. When a bedridden state is attained, the muscles are further kept from moving, and secondary disuse atrophy of muscles is resulted, thereby muscular atrophy and muscle weakness being accelerated. The symptoms of bulbar palsy are symptoms based on the signs of muscular atrophy and muscle weakness in the laryngopharyngeal muscles, tongue, masseteric muscles, facial muscles and the like, and results in the disorder of speech based on phonation disorder and impairment of speech (obscureness in word intelligibility, and the like), or difficulties in swallowing. Eventually, a state of having difficulties in oral intake is attained. In the symptoms of pyramidal tract, the muscle tension in the extremities becomes stronger, and there occurs motor paralysis (spastic paralysis) accompanied by an abnormal increase in muscle tonus, such as difficulties in moving with the muscular hypertonus. In the ALS, the degree and progress of the various symptoms may widely vary, but the prognosis is very poor. Thus, ALS disease progression is relatively fast, and finally respiratory failure due to respiratory muscle paralysis is brought, such that usually death occurs in 2 to 3 years unless an artificial respirator is used. At present, prolongation of life itself has been made possible by respiratory management with artificial respirator after tracheotomy. However, there still are problematic factors such as a severe decrease in the "Quality of Life (QOL)" of the patient, economic insecurity, and insufficient number of caregivers (i.e., scarce manpower) for home care, imposing critical social obstacles and suffering to the patient as well as to the entire family members. Moreover, since the patient's consciousness is maintained normal to the final days and generally intelligence level is also not affected, the patient is put under a cruel situation in which the patient must face the fear of death all the time. Thus, it is expected that by using the therapeutic agent of the present invention, these clinical conditions of ALS may be improved, the period to the time point of using an artificial respirator may be extended, and the time period for possibly maintaining the "QOL" of the patient may be lengthened.

The route of administration for the medicine of the present invention is not particularly limited, and the medicine can be administered orally or parenterally. Examples of the parenteral administration include intrathecal, intravenous, intraarterial, intramuscular, subcutaneous or intradermal injection, inhalation, intrarectal or intranasal administration, as well as nasal instillation, ear instillation, ocular instillation, external administration, and the like.

In regard to the medicine of the present invention, the above-described compounds, which are active ingredients, may be administered alone to the patient, but preferably, the compounds is administered as preparations in the form of a pharmaceutical composition containing the active ingredient and a pharmaceutically acceptable additive. The pharmaceutically acceptable additive includes an excipient, a disintegrant or disintegration aid, a binding agent, a lubricant, a coating agent, a colorant, a diluent, a base, a solubilizing agent or dissolution aid, an isotonic agent, a pH adjusting agent, a stabilizer, a propellant, an adhesive, and the like.

The preparation appropriate for oral administration includes tablet, capsule, powder, fine granule, granule, solution, syrup and the like. The preparation appropriate for parenteral administration includes injectable preparation, drops, suppository, inhalant, nasal drops, ear drops, eye drops, external preparation including adhesive patch, ointment, cream, gel, lotion, spray, and the like.

In the preparation appropriate for oral administration, an additive may be used including: an excipient such as glucose, lactose, D-mannitol, starch or crystalline cellulose; a disintegrant or disintegration aid such as carboxymethylcellulose, starch or carboxymethylcellulose calcium; a binding agent such as hydroxypropylcellulose, hydroxypropylmethylcellulose, polyvinylpyrrolidone or gelatin; a lubricant such as magnesium stearate or talc; a coating agent such as hydroxypropylmethylcellulose, sucrose, polyethylene glycol or titanium oxide; and a base such as petrolatum, liquid paraffin, polyethylene glycol, gelatin, kaolin, glycerin, purified water or hard fat. An additive may also be used in the preparation appropriate for injection, drops, nasal drops, ear drops or eye drops, including: a solubilizing agent or dissolution aid for an aqueous injection solution or a ready-to-use type injection solution such as distilled water for injection, physiological saline or propylene glycol; an isotonic agent such as glucose, sodium chloride, D-mannitol or glycerin; and a pH adjusting agent such as an inorganic acid, an organic acid, an inorganic base or an organic base. In the preparation appropriate for suppository, a base such as polyethylene glycol, lanolin, cacao fat or fatty acid triglyceride, and optionally additives such as surfactants such as nonionic surfactants, can be used.

In the preparation appropriate for ointment, a commonly used additive such as a base, a stabilizer, a wetting agent, a preservative or the like is optionally used. The base includes liquid paraffin, white petrolatum, bleached beeswax, octyldodecyl alcohol, paraffin, and the like. The preservative includes methyl paraoxybenzoate, ethyl paraoxybenzoate, propyl paraoxybenzoate, and the like.

The preparations appropriate for adhesive patch includes a preparation formed by applying the above-described ointment, cream, gel, paste or the like onto a commonly used support using a standard method. As the support, a woven or non-woven fabric formed from cotton, staple fibers or chemical fibers, and a film or foam sheet of flexible vinyl chloride, polyethylene, polyurethane or the like, are preferably used.

The amount of administration of the medicine of the present invention can be appropriately selected depending on various conditions such as the progress or the degree of symptoms of the disease, or the age or body weight of the patient.

EXAMPLES

Hereinafter, the present invention will be described in detail by way of Examples, but the present invention is not intended to be limited to these Examples by any means.

I. Materials and Methods

1. Drug

The following four kinds of xanthine dehydrogenase inhibitors were used.

Namely, these four kinds of 1-[3-cyano-4-(2,2-dimethylpropoxy)phenyl]-1H-pyrazole-4-carboxylic acid (compound (a)), 4-(5-pyridin-4-yl-1H-[1,2,4]triazol-3-yl)pyridine-2-carbonitrile (compound (b)), 2-[3-cyano-4-(2-methylpropoxy)phenyl]-4-methyl-5-thiazolecarboxylic acid (compound (c)) and allopurinol were used.

1) The procedure of concentration adjustment, and the amount and the procedure of administration of the compound (a) were as described below. As a base, 0.5% methylcellulose is prepared. 5 mg of the compound (a) is pulverized in an agate mortar, and then a small amount of 0.5% methylcellulose is added to form a complete suspension. Subsequently, a small amount of 0.5% methylcellulose is added gradually, so that finally 5 mg of the compound (a) is suspended in 10 mL of 0.5% methylcellulose. A sample of 5 mg of compound (a)/10 mL of 0.5% methylcellulose (5 mg/10 mL) was prepared by the above-described procedure, and thus the compound (a) was orally administered once a day in a dose of 5 mg per kg of the mouse body weight (5 mg/kg).

2) The procedure of concentration adjustment, and the amount and the procedure of administration of the compound (b) were similar to those used for the compound (a). A sample of 5 mg of compound (b)/10 mL of 0.5% methylcellulose (5 mg/10 mL) was prepared by the above-described procedure, and thus the compound (b) was orally administered once a day in a dose of 5 mg per kg of the mouse body weight (5 mg/kg).

3) The procedure of concentration adjustment, the amount and the procedure of administration of the compound (c) were similar to those used for the compound (a). A sample of 5 mg of compound (c)/10 mL of 0.5% methylcellulose (5 mg/10 mL) was prepared by the above-described procedure, and thus the compound (c) was orally administered once a day in a dose of 5 mg per kg of the mouse body weight (5 mg/kg).

4) The procedure of concentration adjustment, the amount and the procedure of administration of allopurinol were similar to those used for the compound (a). A sample of 5 mg of allopurinol/10 mL of 0.5% methylcellulose (5 mg/10 mL) was prepared by the above-described procedure, and thus allopurinol was orally administered once a day in a dose of 5 mg per kg of the mouse body weight (5 mg/kg).

5) As a placebo, only the base, 0.5% methylcellulose, was orally administered once a day in a dose of 10 mL per kg of the mouse body weight (10 mL/kg), that is, in the same volume as that of the base for the drug-administered mice.

6) In the oral administration, the volume of the drug suspension was precisely measured with a plastic syringe. A gastric tube for mouse was directly connected to the plastic syringe to certainly administer the drug perorally and transesophageally.

2. Experimental Animal

As the experimental animal, male transgenic mice overexpressing a high copy number (25 copies) of mutated human SOD1 gene with a G93A point mutation, i.e., B6SJL-TgN[SOD1-G93A]1Gur (G1H-G93A transgenic mice, JR2726; Hemizygote) (Gurney M E, et al., Science, 264, 1772-1775, 1994), were purchased from Jackson Laboratory (Bar Harbor, USA) and used. At the same time, wild-type male mice from the same litter, B6SJL-TgN[SOD1-G93A]1Gur (Wild-type), were also purchased from Jackson Laboratory and used.

3. Clinical Symptomatological Evaluation of Mouse

The mice were subjected to a clinical symptomatological evaluation everyday. The clinical symptomatological evaluation was performed from one week after the arrival from Jackson Laboratory. The clinical symptomatological evaluation of the mice was performed based on the following criteria: Stage 0=The mouse can show normal walking with the same agile movements as the wild-type mice from the same litter; Stage 1=The mouse shows any one or more of clinical symptoms selected from lack of agility, jittering, limp tail, and slow walking accompanied by muscle weakness; Stage 2=The mouse shows unilateral and/or bilateral, incomplete but definite hindlimb paresis without weakness of forelimbs; Stage 3=The mouse shows severe bilateral hindlimb paralysis while having nearly normal forelimbs; Stage 4=The mouse shows severe and almost complete bilateral hindlimb paralysis accompanied by unilateral and/or bilateral forelimb incomplete paresis; and Stage 5=The mouse shows severe and almost complete quadriplegia, or is in the moribund state. The day of onset, the survival period and the disease period were indicated by the number of days. In regard to the indication of the number of days of the disease period, one day (one disease day) corresponds to within 24 hours from the onset (the "onset" is determined by the observation of the clinical symptomatological evaluation stage 1), and two days (two disease days) corresponds to more than 24 hours after and within 48 hours from the onset. Subsequent disease days after the onset were determined in the same manner.

4. Exercise Tolerance Test for Mouse

The following five kinds of exercise tolerance tests were conducted every fifth day from the $70^{th}$ day after birth to evaluate the ability to exercise in the respective exercise tolerance tests. That is, the days for the exercise tolerance tests were every fifth days, such as the $70^{th}$ day, $75^{th}$ day, $80^{th}$ day, $85^{th}$ day and so on, after birth. The exercise tolerance tests were conducted throughout the survival period, and the post-mortem evaluation was based on the definitions of the following five kinds of exercise tolerance tests.

1) Extension Reflex Test

As for extension reflex, extension of the hindlimbs is normally observed when a mouse is suspended in the air by its tail.

The evaluation of extension reflex test of the mice was performed based on the following criteria: Score 0=Extension reflex is recognized in both of the hindlimbs; Score 1=Extension reflex is recognized only one hindlimb; and Score 2=Extension reflex is not recognized in both of the hindlimbs. The post-mortem evaluation of the extension reflex test is defined as score 2.

2) Inclined Plane Test

The apparatus used in the inclined plane test is an apparatus allowing a wooden board to be fixed at the respective angles of 45°, 65° and 80° from a horizontal plane. A mouse is placed in the posture of head-up position on the wooden board inclined at each angle and the mouse is allowed to maintain this position for 5 seconds without falling downward. In the evaluation method of the inclined plane test for each mouse, the number of seconds ($T_A$ seconds: 5 seconds or less) during which the position could be maintained without falling downward is measured at each of the angles (A) of 45°, 65° and 80°, and then the total sum value of the products of the angle (A) and the number of seconds ($T_A$) during which the position could be maintained: $\Sigma$ [Angle(A)×Time ($T_A$)] is calculated. Since a normal mouse is capable of maintaining the position on the wooden board inclined to the respective angles for 5 seconds, the sum value of $\Sigma$ [Angle(A)×Time ($T_A$)] will be 80×5+65×5+45×5=950. The evaluation of the inclined plane test for the mouse was performed based on the following criteria: Score 0=950; Score 1=over 550 to less than 950; Score 2=over 225 to 550; and Score 3=225 and below. The post-mortem evaluation of the inclined plane test is defined as score 3.

3) Footprint Test

Both hindlimbs of a mouse are dipped in a black ink bottle, and then the mouse is allowed to walk on white paper. The footprints of the two hindlimbs of the mouse after the walking are analyzed. The evaluation of the mouse footprint test was performed based on the following criteria: Score 0=The length of stride for both hindlimbs is over 6 cm without dragging; Score 1=The length of stride for both hindlimbs is not exceeding 6 cm without dragging; Score 2=The mouse shows the walk while dragging only one hindlimb; Score 3=The mouse exhibits the walk while dragging both hindlimbs; and Score 4=The mouse is in the state of being unable to walk. The post-mortem evaluation of the footprint test is defined as score 4.

4) Rotarod Test

The apparatus used in the Rotarod test (Rota Rod Treadmill type 7600, Ugo Basile Co., Milano, Italy) is a rotating axle having a diameter of 3.6 cm, and this rotating axle is set up so as to have 16 revolution per minute (one rotation: 3.75 seconds). The period for which a mouse can remain on a rotating axle without falling is measured. The evaluation of the rotarod test for the mouse was performed based on the following criteria: Score 0=The time exceeds 60 seconds; Score 1=The time is more than 30 seconds and 60 seconds or less; Score 2=The time is more than 4 seconds and 30 seconds or less; and Score 3=The time is 4 seconds or less. The post-mortem evaluation of the rotarod test is defined as score 3.

5) Beam Balance Test

The apparatus used in the beam balance test is constructed by maintaining a wooden beam having a diameter of 1.5 cm horizontally, and installing platforms which serve as footholds, on the respective sides in a distance of 30 cm. A mouse is placed on the platform on one side, and the time taken by the mouse to cross over the beam which is 30 cm in length and to arrive at the platform on the opposite side is measured. The evaluation of the beam balance test for the mouse was performed based on the following criteria: Score 0=The time is 10 seconds or less; Score 1=The time is more than 10 seconds to 15 seconds; and Score 2=The time is more than 15 seconds, or the mouse falls down. The post-mortem evaluation of the beam balance test is defined as score 2.

5. Design of Experiment Based on Administration of Placebo or Medicament

The mice were divided into seven experimental groups, to which a placebo, the compound (a), compound (b), compound (c) or allopurinol was administered. That is, the seven groups consist of: an experimental group administered with placebo; a treatment experimental group administered with compound (a) before onset; a treatment experimental group administered with compound (a) after onset; a treatment experimental group administered with compound (b) before onset; a treatment experimental group administered with compound (c) before onset; a treatment experimental group administered with compound (c) after onset; and a treatment group administered with allopurinol before onset. Details of the respective groups will be described in the following.

1) Experimental Group Administered with Placebo:

Ten G1H-G93A transgenic mice and ten wild-type mice from the same litter were used. The two groups were both orally administered with 0.5% methylcellulose (10 mL/kg) as a placebo, from the $80^{th}$ day after birth. In the duration of oral administration, the placebo was administered everyday until the G1H-G93A transgenic mice had reached the state of quadriplegia and the moribund state. The ten wild-type littermates were orally administered everyday with 0.5% methylcellulose (10 mL/kg), as a placebo. The ten wild-type mice from the same littermates which were orally administered with 0.5% methylcellulose (10 mL/kg) were used as a normal control group.

2) Treatment Experimental Group Administered with Compound (a)

(1) Treatment Experimental Group Administered with Compound (a) Before Onset:

Ten G1H-G93A transgenic mice were used. From the $80^{th}$ day after birth, 5 mg/kg of the compound (a) was orally administered everyday. The dosing period was the period of time taken until each of the G1H-G93A transgenic mice showed quadriplegia and reached the moribund state.

(2) Treatment Experimental Group Administered with Compound (a) after Onset:

Ten G1H-G93A transgenic mice were used. The onset of the disease was determined by observing the symptoms of stage 1 of the clinical symptomatological evaluation (i.e., any one or more of clinical symptoms selected from lack of agility, jittering, limp tail, and slow walking accompanied by muscle weakness), and from the onset, 5 mg/kg of the compound (a) was orally administered everyday. The duration of the treatment was the period of time taken until each of the G1H-G93A transgenic mice showed quadriplegia and reached the moribund state.

3) Treatment Experimental Group Administered with Compound (b)

(1) Treatment Experimental Group Administered with Compound (b) Before Onset:

Ten G1H-G93A transgenic mice were used. From the $80^{th}$ day after birth, 5 mg/kg of the compound (b) was orally administered everyday. The dosing period was the period of time taken until each of the G1H-G93A transgenic mice showed quadriplegia and reached the moribund state.

4) Treatment Experimental Group Administered with Compound (c)

(1) Treatment Experimental Group Administered with Compound (c) Before Onset:

Ten G1H-G93A transgenic mice were used. From the $80^{th}$ day after birth, 5 mg/kg of the compound (c) was orally administered everyday. The duration of the treatment was the period of time taken until each of the G1H-G93A transgenic mice showed quadriplegia and reached the moribund state.

(2) Treatment Experimental Group Administered with Compound (c) after Onset:

Ten G1H-G93A transgenic mice were used. The onset of the disease was determined by observing the symptoms of stage 1 of the clinical symptomatological evaluation, and from the day including this time point, 5 mg/kg of the compound (c) was orally administered everyday. The dosing period was the period until disease endpoint (stage 5).

5) Treatment Experimental Group Administered with Allopurinol (1) Treatment Experimental Group Administered with Allopurinol Before Onset:

Ten G1H-G93A transgenic mice were used. From the $80^{th}$ day after birth, 5 mg/kg of allopurinol was orally administered everyday. The dosing period is the period until each of the G1H-G93A transgenic mice showed quadriplegia and reached the moribund state.

6. Histopathological Study

The mouse supplied to the experiment is anesthetized by intraperitoneal injection of pentobarbital sodium in an amount of 1 mL per kg of the mouse body weight. After confirming that the mouse is completely under anesthesia, laparotomy and thoracotomy are performed, and blood is completely removed from the visceral organs of the whole body by perfusion of physiological saline at 37° C. via the left ventricle and aorta. The complete removal of blood from the visceral organs of the whole body is carried out by confirming complete removal of the blood of the aorta in the thoracic part and abdominal part, mesenteric arteries, liver, kidneys, and small arteries on the surfaces of the stomach, small intestine and large intestine under direct visual inspection. Subsequently, perfusion of 50 mL of physiological saline at 37° C. is performed. Immediately thereafter, the perfusion is performed with a fixative (4% paraformaldehyde supplemented with 0.1 M cacodylate buffer, pH 7.4). The spinal cord is removed and re-fixed with the same fixative for 18 hours. After the fixation of spinal cord tissue, each spinal cord segments is cut out to examine the spinal cord tissue. For the detailed analyses of spinal cord tissues, two segments of the cervical spinal cord (upper and lower cervical segments), three segments of the thoracic spinal cord (upper, middle, and lower thoracic segments), and two segments of lumbar spinal cord (upper and lower lumbar segments) were cut out to provide seven segments in total. Each spinal cord segments are respectively embedded in paraffin to produce paraffin blocks, and then cut into paraffin sections having a thickness of 5 μm using a microtome. The paraffin sections are subjected to hematoxylin and eosin (HE) staining.

For a quantitative analysis, serial 25 paraffin sections having a thickness of 5 μm were produced in series from the respective segment paraffin blocks of the spinal cord, and the 1$^{st}$ section, 7$^{th}$ section, 13$^{th}$ section, 19$^{th}$ section and 25$^{th}$ section were selected and subjected to HE staining. Specifically, paraffin sections were selected such that one paraffin section was taken at a 25 μm interval, and 5 HE preparations were produced from a single spinal cord segments. Therefore, 10 HE preparations from two areas for the entire cervical spinal cord, 15 HE preparations from three areas for the entire thoracic spinal cord, and 10 HE preparations from two areas for the entire lumbar spinal cord, were produced.

In order to calculate the number of motor neurons in the anterior horn, all of the HE stained sections were observed under a light microscope (BX41: Olympus Corp., Tokyo, Japan) equipped with a 3CCD digital color camera system for the microscope (FX380: Olympus Corp., Tokyo, Japan). Subsequently, photographs of the anterior horn region (corresponding to VII, VIII and IX Rexed areas) in the HE stained sections of the respective myelomere tissues of the spinal cord were taken, and the images were analyzed using an image analysis-filing software (FLVFS-LS Ver. 1.12: Olympus Corp., Tokyo, Japan). In regard to the definition of the motor neuron in the anterior horn of spinal cord (spinal cord anterior horn cells), cells in the HE stained sections, which have a nucleus carrying a definite nucleolus and contain a cell body having a diameter of 25 μm or more, were selected as the spinal cord anterior horn cells (Klivenyi P, et al., Nature Med 1999; 5:347-351, Kong J & Xu Z, J Neurosci 1998; 18:3241-3250, and Stephens B, et al., Neuropathol Appl Neurobiol 2001; 27:352-361). Based on this definition, the number of spinal cord anterior horn cells was counted for each of the HE stained sections. The respective numbers of spinal cord anterior horn cells in the cervical spinal cord, thoracic spinal cord and lumbar spinal cord of one mouse was calculated from the total number of spinal cord anterior horn cells in five HE stained sections. As for the number of spinal cord anterior horn cells in the cervical cord, the total number of spinal cord anterior horn cells was measured as the sum of the numbers of spinal cord anterior cells in ten HE stained sections from the two different areas of cervical spinal cord, and then the number of spinal cord anterior horn cells per five sections was calculated. As for the number of spinal cord anterior horn cells in the thoracic cord, the total number of spinal cord anterior horn cells was measured as the sum of the numbers of spinal cord anterior cells in 15 HE stained sections from the three different areas of thoracic spinal cord, and then the number of spinal cord anterior horn cells per five sections was calculated. As for the number of spinal cord anterior horn cells in the lumbar cord, the total number of spinal cord anterior horn cells was measured as the sum of the numbers of spinal cord anterior cells in 10 HE stained sections from the two different areas of lumbar spinal cord, and then the number of spinal cord anterior horn cells per five sections was calculated.

7. Statistical Analysis Method

In regard to the results of the clinical symptomatological evaluation, the day of onset, the survival period (days taken to show quadriplegia and to reach the moribund state), the disease period (days taken to show quadriplegia and to reach the moribund state, from the day of onset), and the time periods for the respective stages of the clinical symptomatological evaluation, were indicated by the average±standard deviation. In regard to the results of the exercise tolerance test, the score values of the respective exercise tolerance tests, including the extension reflex test, inclined plane test, footprint test, rotarod test and beam balance test, were indicated by the average±standard deviation. In regard to the results of the histopathological study, the calculated numbers of spinal cord anterior horn cells were indicated by the average±standard deviation.

The statistical analyses were all performed using Statview for Macintosh (Ver. 5.0, SAS Institute, Inc., California, USA). In the significance test, Mann-Whitney's U test, and the log-rank test of the Kaplan-Meier method were used. Criterion of statistically significant difference is risk rate of $P<0.05$.

II. Results

1. Results of Clinical Symptomatological Evaluation for Respective Experimental Groups Administered with Placebo or Drugs 1) Experimental Group Administered with Placebo:

The day of onset for the G1H-G93A transgenic mice in the experimental group administered with placebo was 99.9±2.4 days, the survival period was 119.7±3.3 days, and the disease period was 20.8±2.3 days (Tables 1A, 2A, 3A and 4A). The time periods for the respective stage numbers in the clinical symptomatological evaluation of the mice from the experimental group administered with placebo were the following: stage 1=6.6±0.7 days; stage 2=5.4±0.8 days; stage 3=4.3±0.8 days; stage 4=2.8±0.6 days; and stage 5=1.7±0.5 days (Tables 1B, 2B, 3B and 4B) (FIG. 1). For the wild-type mice from the same littermates, which were the normal control group for the experimental group administered with placebo, all of the 10 animal samples came under stage 0 throughout the whole process in the clinical symptomatological evaluation.

Figure 2:
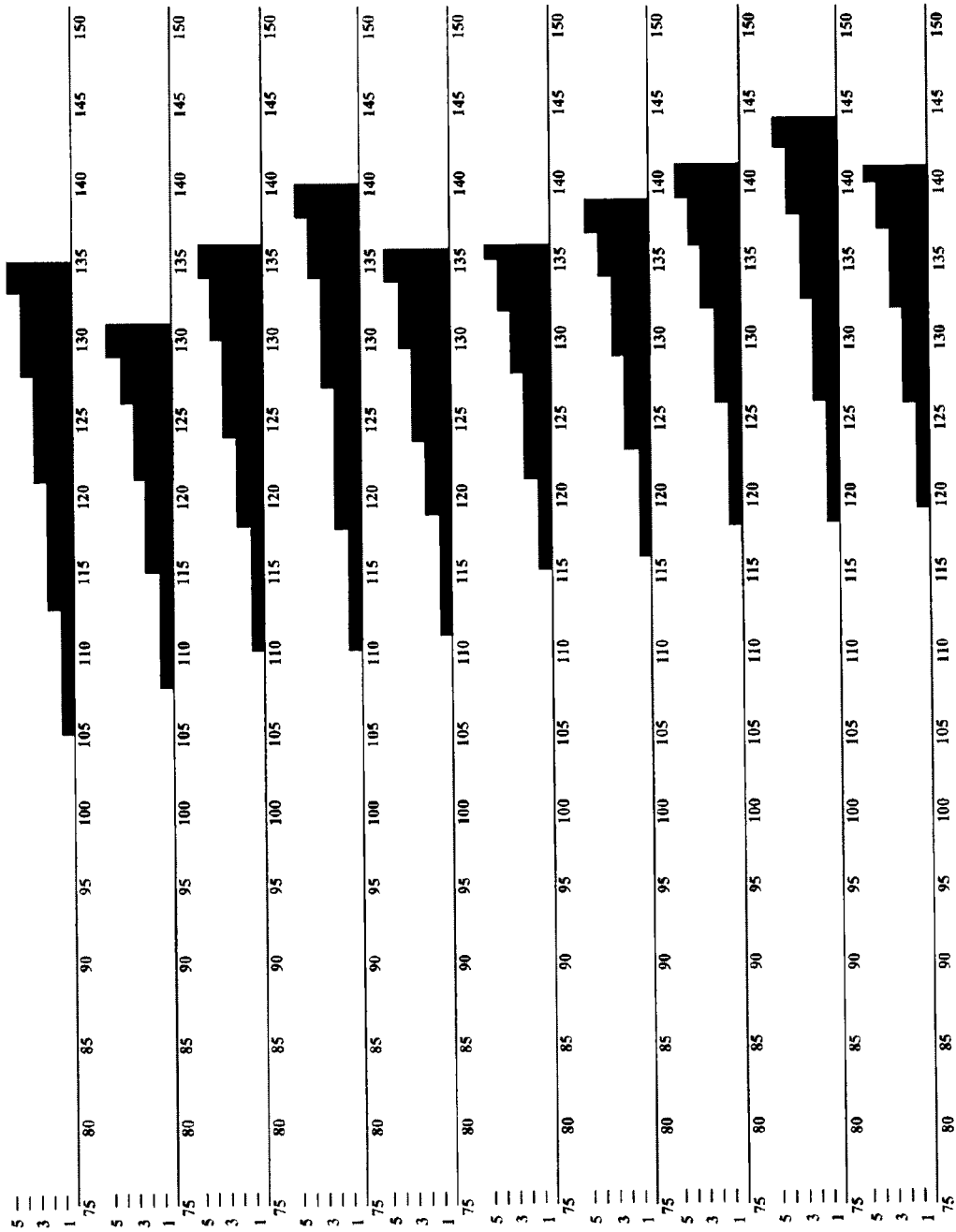
FIG. 2 is a diagram showing a clinical symptomatological evaluation of the respective G1H-G93A transgenic mice in a treatment experimental group administered with compound (a) before onset. The vertical axis represents the degree of clinical symptomatological stage, and the horizontal axis represents days after birth.

2) Treatment Experimental Group Administered with Compound (a) Before Onset:

The day of onset for the G1H-G93A transgenic mice in the treatment experimental group administered with compound (a) before onset was 113.0±4.8 days, the survival period was 136.9±3.8 days, and the disease period was 24.9±3.1 days (Table 1A). The time periods for the respective stage in the clinical symptomatological evaluation of the mice from the treatment experimental group administered with compound (a) before onset were the following: stage 1=7.5±0.7 days; stage 2=6.6±1.2 days; stage 3=5.4±1.1 days; stage 4=3.6±0.7 days; and stage 5=1.8±0.4 days (Tables 1B) (FIG. 2).

Figure 3:
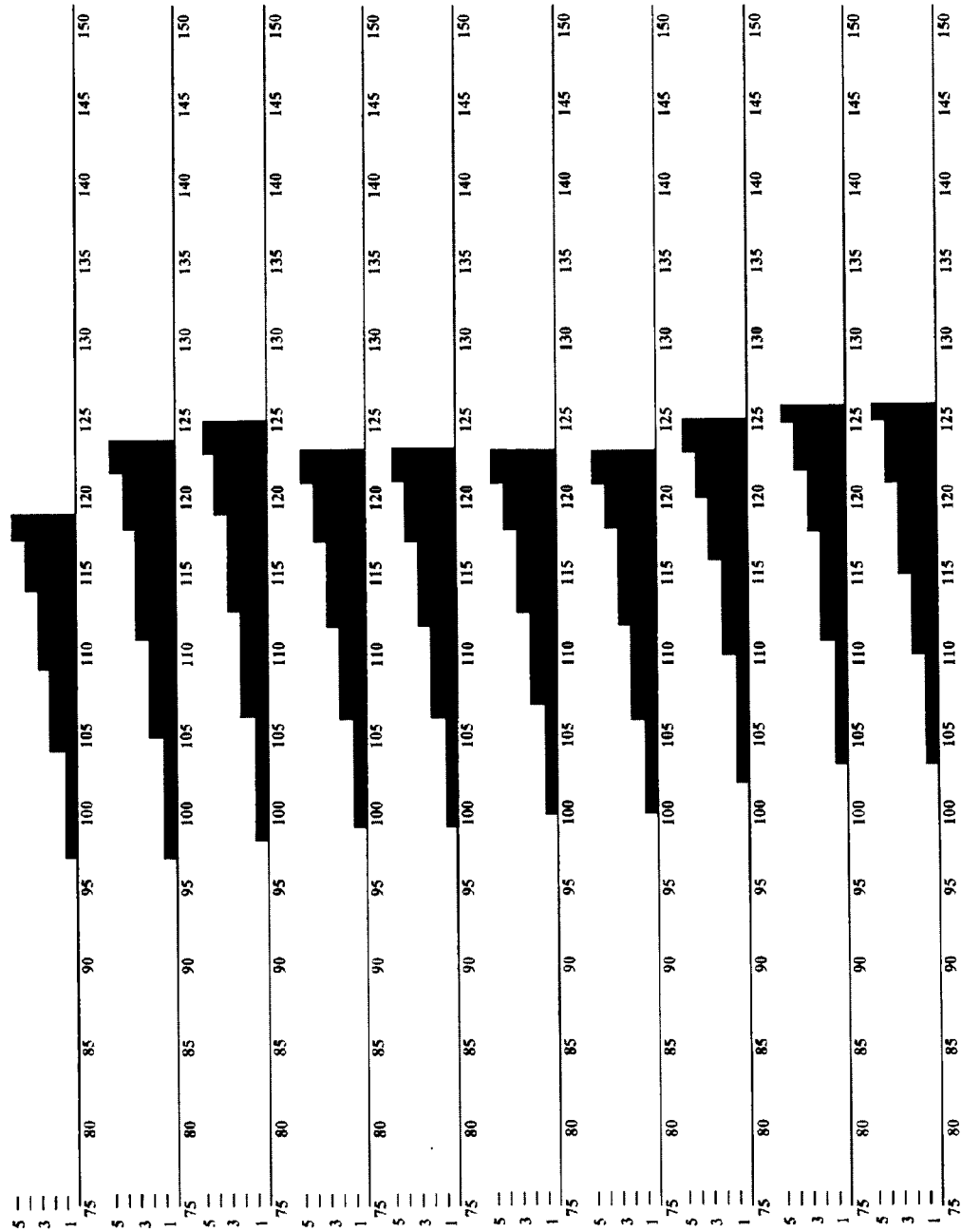
FIG. 3 is a diagram showing a clinical symptomatological evaluation of the respective G1H-G93A transgenic mice in a treatment experimental group administered with compound (a) after onset. The vertical axis represents the degree of clinical symptomatological stage, and the horizontal axis represents days after birth.

3) Treatment Experimental Group Administered with Compound (a) after Onset:

The day of onset for the G1H-G93A transgenic mice in the treatment experimental group administered with compound (a) after onset was 99.8±2.4 days, the survival period was 122.7±2.1 days, and the disease period was 23.9±1.7 days (Table 2A). The time periods for the respective stage in the clinical symptomatological evaluation of the mice from the treatment experimental group administered with compound (a) after onset were the following: stage 1=7.3±0.7 days; stage 2=6.0±0.7 days; stage 3=5.3±0.9 days; stage 4=3.5±0.5 days; and stage 5=1.8±0.4 days (Tables 2B) (FIG. 3).

Figure 4:
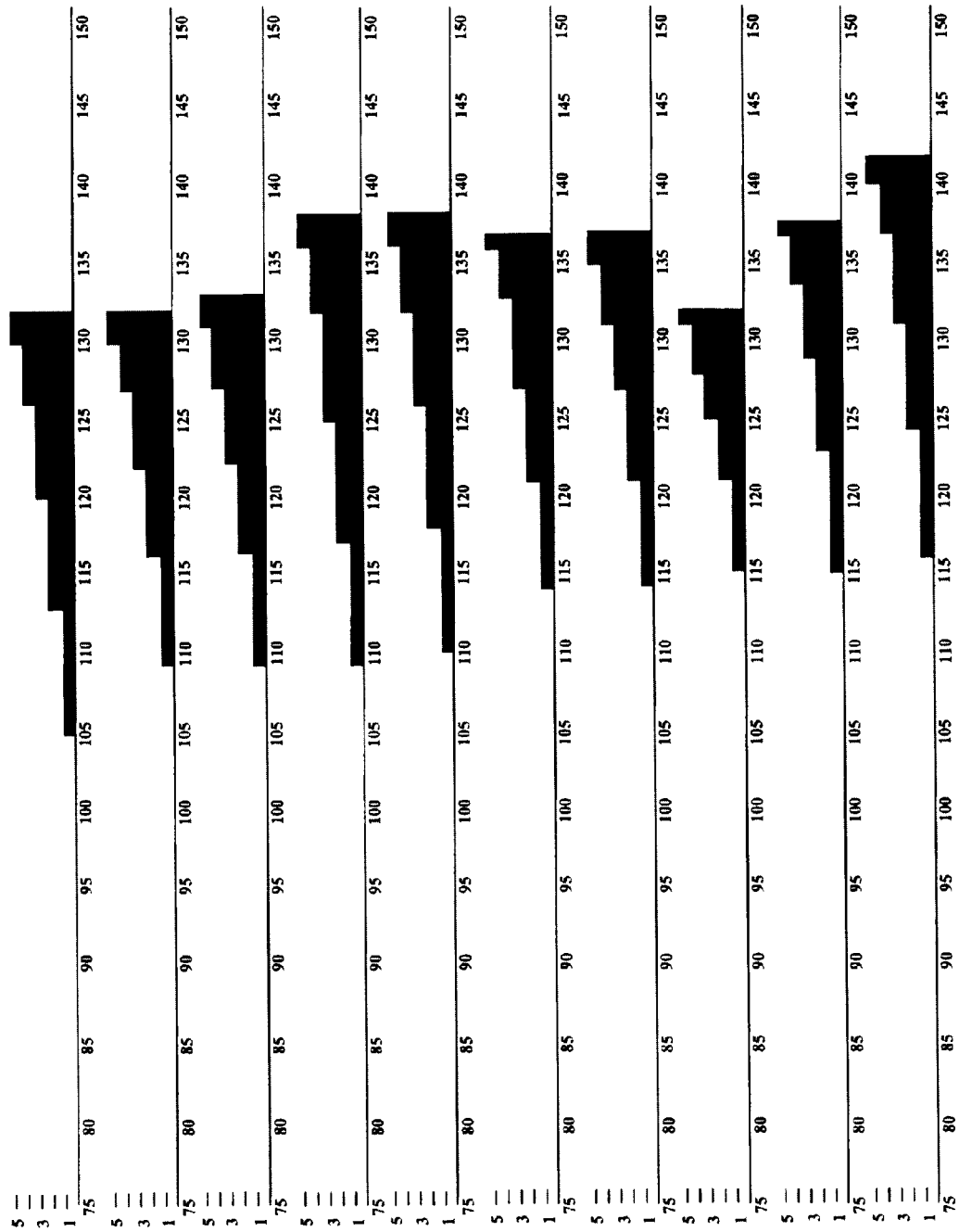
FIG. 4 is a diagram showing a clinical symptomatological evaluation of the respective G1H-G93A transgenic mice in a treatment experimental group administered with compound (b) before onset. The vertical axis represents the degree of clinical symptomatological stage, and the horizontal axis represents days after birth.

4) Treatment Experimental Group Administered with Compound (b) Before Onset:

The day of onset for the treatment experimental group administered with compound (b) before onset was 111.6±3.7 days, the survival period was 134.9±3.4 days, and the disease period was 24.3±3.4 days (Table 3A). The time periods for the respective stage numbers in the clinical symptomatological evaluation of the mice from the treatment experimental group administered with compound (b) before onset were the following: stage 1=7.4±0.7 days; stage 2=6.4±1.2 days; stage 3=5.3±1.2 days; stage 4=3.5±0.5 days; and stage 5=1.7±0.5 days (Tables 3B) (FIG. 4).

Figure 5:
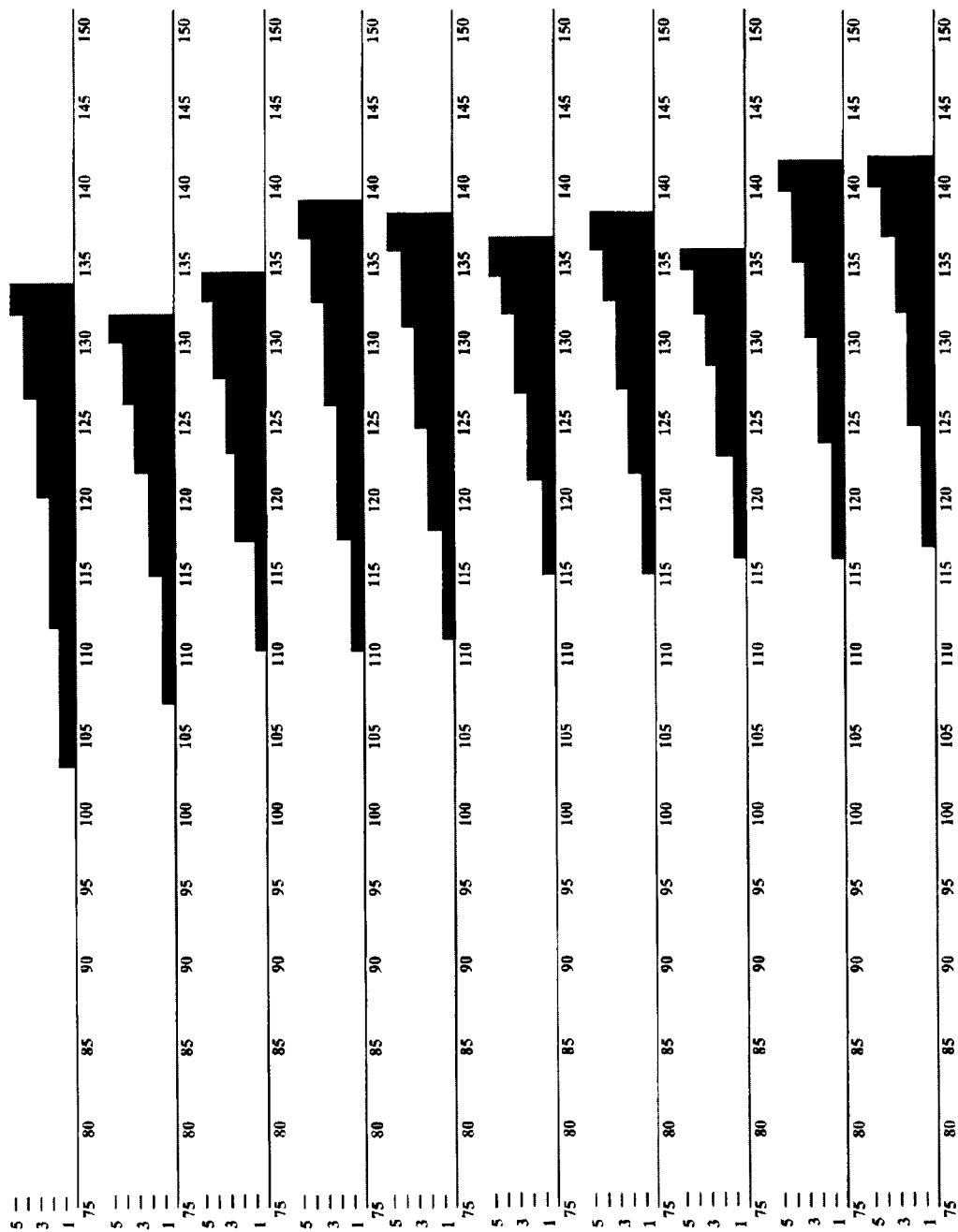
FIG. 5 is a diagram showing a clinical symptomatological evaluation of the respective G1H-G93A transgenic mice in a treatment experimental group administered with compound (c) before onset. The vertical axis represents the degree of clinical symptomatological stage, and the horizontal axis represents days after birth.

5) Treatment Experimental Group Administered with Compound (c) Before Onset:

The day of onset for the G1H-G93A transgenic mice in the treatment experimental group administered with compound (c) before onset was 112.0±4.6 days, the survival period was 136.4±3.3 days, and the disease period was 25.4±3.2 days (Table 4A). The time periods for the respective stage in the clinical symptomatological evaluation of the mice from the treatment experimental group administered with compound (c) before onset were the following: stage 1=7.5±0.9 days; stage 2=6.7±1.2 days; stage 3=5.4±1.1 days; stage 4=3.9±1.1 days; and stage 5=1.9±0.3 days (Tables 4B) (FIG. 5).

Figure 17:
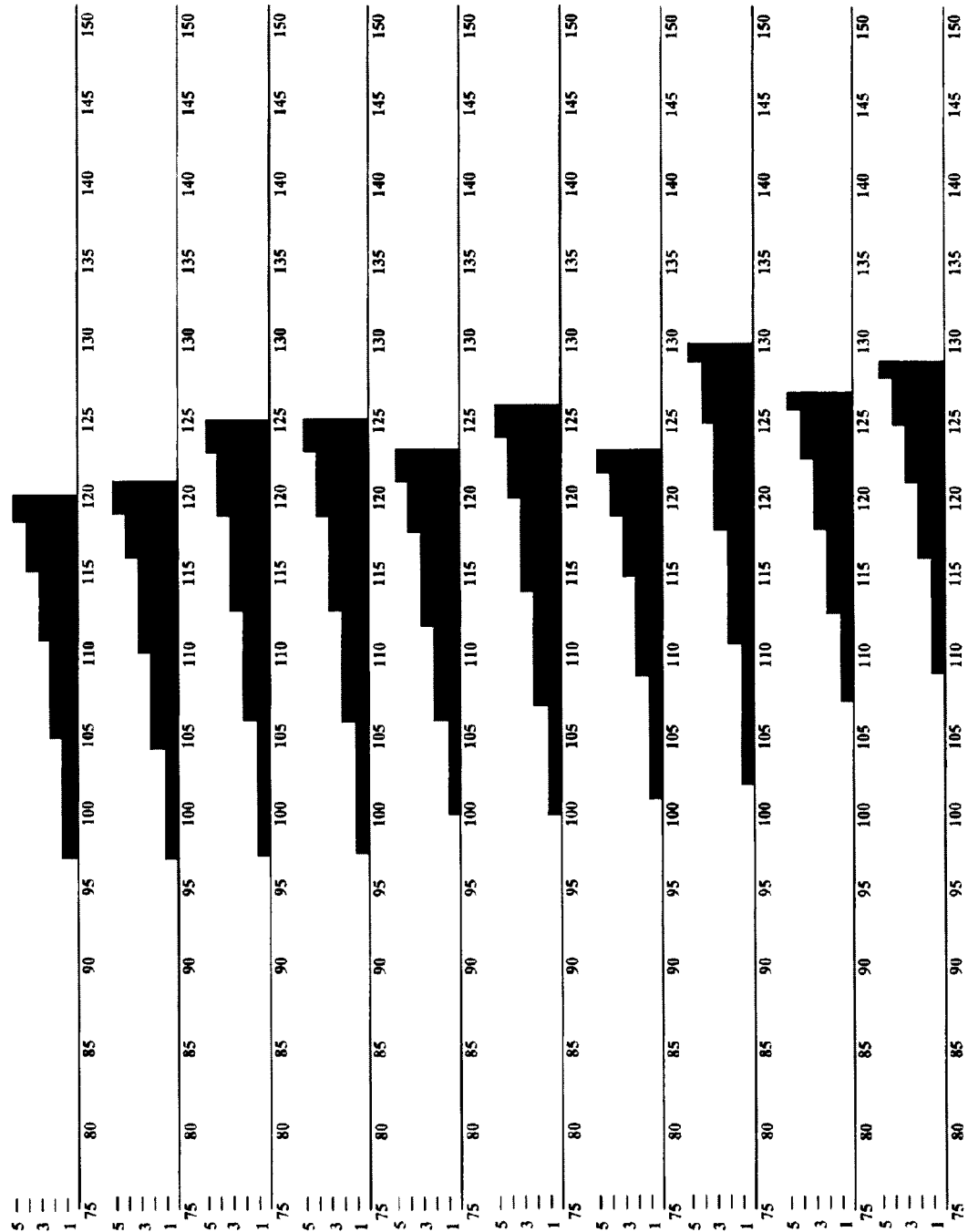
FIG. 17 is a diagram showing a clinical symptomatological evaluation of the respective G1H-G93A transgenic mice in the treatment experimental group administered with compound (c) after onset. The vertical axis represents the degree of clinical symptomatological stage, and the horizontal axis represents days after birth.

6) Treatment Experimental Group Administered with Compound (c) after Onset:

The day of onset for the G1H-G93A transgenic mice in the treatment experimental group administered with compound (c) after onset was 100.7±4.3 days, the survival period was 123.9±3.2 days, and the disease period was 24.2±3.2 days (Table 5A). The time periods for the respective stage in the clinical symptomatological evaluation of the mice from the treatment experimental group administered with compound (c) after onset were the following: stage 1=7.6±1.2 days; stage 2=6.2±0.8 days; stage 3=5.4±1.1 days; stage 4=3.5±0.5 days; and stage 5=1.5±0.5 days (Tables 5B) (FIG. 17).

Figure 20:
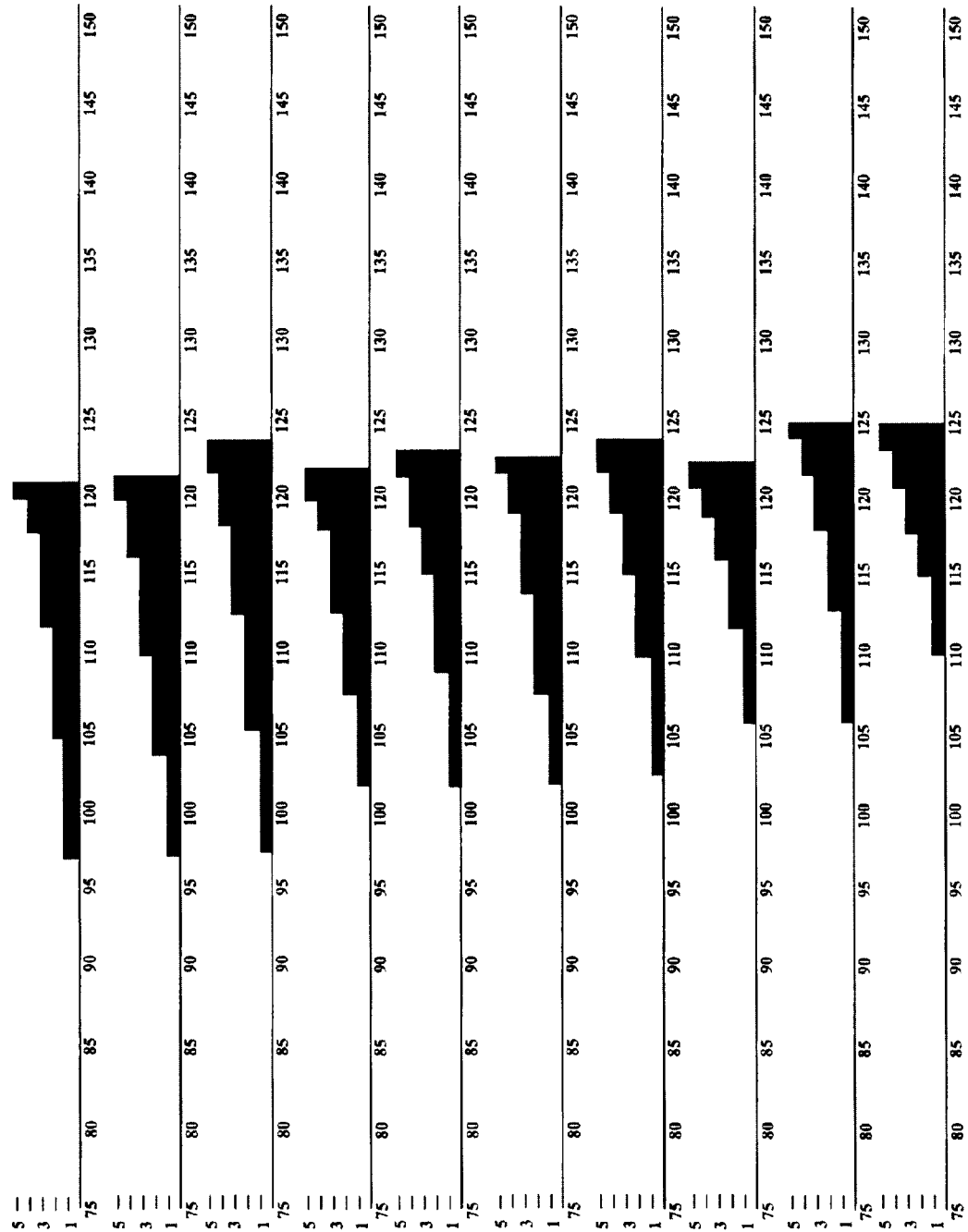
FIG. 20 is a diagram showing a clinical symptomatological evaluation of the respective G1H-G93A transgenic mice in the treatment experimental group administered with allopurinol before onset. The vertical axis represents the degree of clinical symptomatological stage, and the horizontal axis represents days after birth.

7) Treatment Experimental Group Administered with Allopurinol Before Onset:

The day of onset for the G1H-G93A transgenic mice in the treatment experimental group administered with allopurinol before onset was 102.2±4.4 days, the survival period was 122.2±1.3 days, and the disease period was 21.0±3.6 days (Table 6A). The time periods for the respective stage in the clinical symptomatological evaluation of the mice from the treatment experimental group administered with allopurinol before onset were the following: stage 1=6.8±1.1 days; stage 2=5.4±1.3 days; stage 3=4.4±1.2 days; stage 4=2.9±0.7 days; and stage 5=1.5±0.5 days (Tables 6B) (FIG. 20).

2. Results of Clinical Symptomatological Analysis on Effectiveness of Drugs

Figure 6:
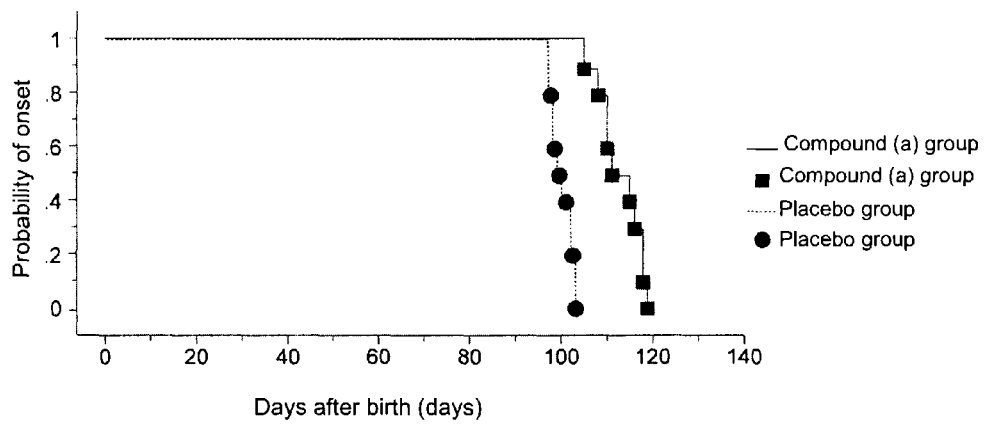
FIG. 6 is a diagram showing the results of a log-rank test of the Kaplan-Meier's method with regard to the day of onset, for the experimental group administered with placebo and the treatment experimental group administered with compound (a) before onset. The vertical axis represents the probability of onset, and the horizontal axis represents days after birth.
Figure 7:
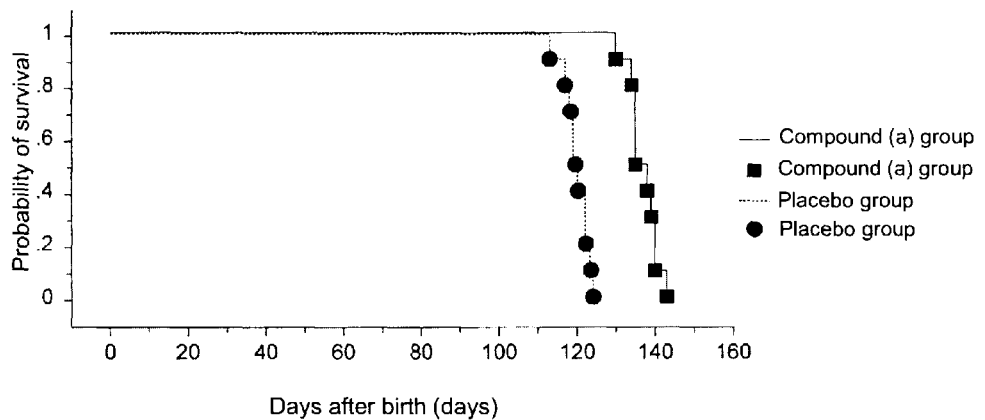
FIG. 7 is a diagram showing the results of a log-rank test of the Kaplan-Meier's method with regard to the survival period, for the experimental group administered with placebo and the treatment experimental group administered with compound (a) before onset. The vertical axis represents the probability of survival, and the horizontal axis represents days after birth.

1) Clinical Symptomatological Effectiveness of Treatment with Administration of Compound (a) Before Onset:

Daily oral administration of 5 mg/kg of compound (a) to G1H-G93A transgenic mice from the $80^{th}$ day after birth resulted in significant delaying of the day of onset (onset delaying effect) (P<0.001, Mann-Whitney's U test), significant extension of the survival period (survival period extending effect) (P<0.001, Mann-Whitney's U test) and significant extension of the disease period (disease period extending effect) (P<0.01, Mann-Whitney's U test), in comparison to the group administered with placebo (Table 1A). Furthermore, the respective data, i.e., the day of onset (FIG. 6), survival period (FIG. 7) and disease period (FIG. 8) for the treatment group administered with compound (a) before onset, were analyzed using to a log-rank test of the Kaplan-Meier method to compare with data from the group administered with placebo. As a result, the date and periods were found to be extended with significant differences. Therefore, it was clearly indicated that the administration of compound (a) before the onset led to the onset delaying effect, survival period extending effect and disease period extending effect. In regard to the time periods for the respective stages of the clinical symptomatological evaluation, the group administered with compound (a) before onset was found to have the extended period of respective stages with significant difference in comparison to the group administered with placebo: stage 1 (P<0.05, Mann-Whitney's U test); stage 2 (P<0.05, Mann-Whitney's U test); stage 3 (P<0.05, Mann-Whitney's U test); and stage 4 (P<0.05, Mann-Whitney's U test) (Table 1B).

TABLE 1

1A

| | N | Day of onset (days) | | Survival period (days) | | Disease period (days) | |
|---|---|---|---|---|---|---|---|
| Group administered with placebo | 10 | 99.9 ± 2.4 | P* | 119.7 ± 3.3 | P* | 20.8 ± 2.3 | P** |
| Group administered with compound (a) before onset | 10 | 113.0 ± 4.8 | | 136.9 ± 3.8 | | 24.9 ± 3.1 | |

N: Number of mice used

P* <0.001, Mann-Whitney's U test

P** <0.01, Mann-Whitney's U test

TABLE 1-continued

1B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 ⎤ P* | 5.4 ± 0.8 ⎤ P* | 4.3 ± 0.8 ⎤ P* | 2.8 ± 0.6 ⎤ P* | 1.7 ± 0.5 |
| Group administered with compound (a) before onset | 10 | 7.5 ± 0.7 ⎦ | 6.6 ± 1.2 ⎦ | 5.4 ± 1.1 ⎦ | 3.6 ± 0.7 ⎦ | 1.8 ± 0.4 |

N: Number of mice used
P* <0.05, Mann-Whitney's U test

Figure 10:
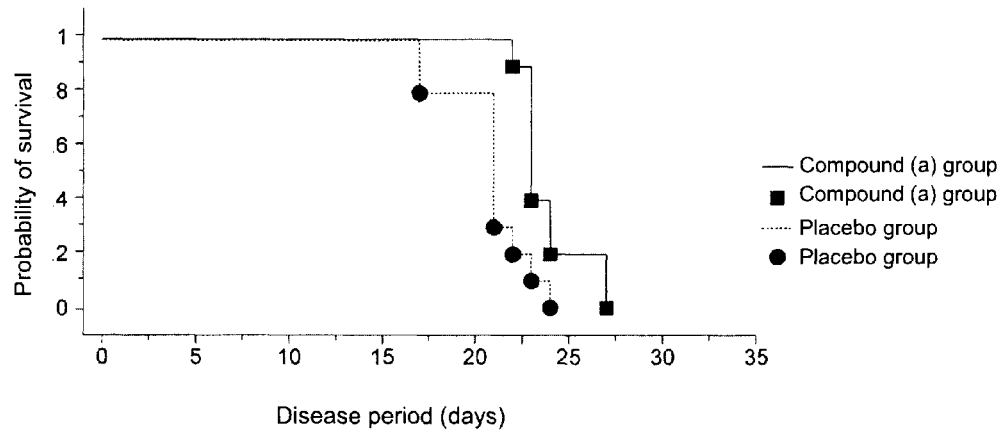
FIG. 10 is a diagram showing the results of a log-rank test of the Kaplan-Meier's method with regard to the disease period, for the experimental group administered with placebo and the treatment experimental group administered with compound (a) after onset. The vertical axis represents the probability of survival, and the horizontal axis represents disease period.

2) Clinical Symptomatological Effectiveness of Administration of Compound (a) after Onset:

Daily oral administration of 5 mg/kg of compound (a) to G1H-G93A transgenic mice from the day of onset resulted in significant extension of the disease period (disease period extending effect) ($P<0.05$, Mann-Whitney's U test), and therefore, significant extension of the survival period (survival period extending effect) ($P<0.005$, Mann-Whitney's U test), in comparison to the group administered with placebo (Table 2A). In addition, the two data, i.e., the survival period (FIG. 9) and disease period (FIG. 10) for the group administered with compound (a) after the onset, were analyzed using a log-rank test of the Kaplan-Meier method to compare with data from the group administered with placebo. As a result, these periods were found to be extended with significant differences. Therefore, it was clearly indicated that the administration of compound (a) after the onset led to the survival period extending effect due to the disease period extending effect. In regard to the time periods for the respective stages of the clinical symptomatological evaluation, the group administered with compound (a) after onset was found to have the extended period of stage 3 ($P<0.05$, Mann-Whitney's U test) and stage 4 ($P<0.05$, Mann-Whitney's U test) with significant differences, in comparison to the group administered with placebo (Table 2B).

TABLE 2

2A

| | N | Day of onset (days) | Survival period (days) | Disease period (days) |
|---|---|---|---|---|
| Group administered with placebo | 10 | 99.9 ± 2.4 | 119.7 ± 3.3 ⎤ P* | 20.8 ± 2.3 ⎤ P** |
| Group administered with compound (a) before onset | 10 | 99.8 ± 2.4 | 122.7 ± 2.7 ⎦ | 23.9 ± 1.7 ⎦ |

N: Number of mice used
P* <0.005, Mann-Whitney's U test
P** <0.05, Mann-Whitney's U test

2B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 | 5.4 ± 0.8 | 4.3 ± 0.8 ⎤ P* | 2.8 ± 0.6 ⎤ P* | 1.7 ± 0.5 |
| Group administered with compound (a) before onset | 10 | 7.3 ± 0.7 | 6.0 ± 0.7 | 5.3 ± 0.9 ⎦ | 3.5 ± 0.5 ⎦ | 1.8 ± 0.4 |

N: Number of mice used
P* <0.05, Mann-Whitney's U test

Figure 11:
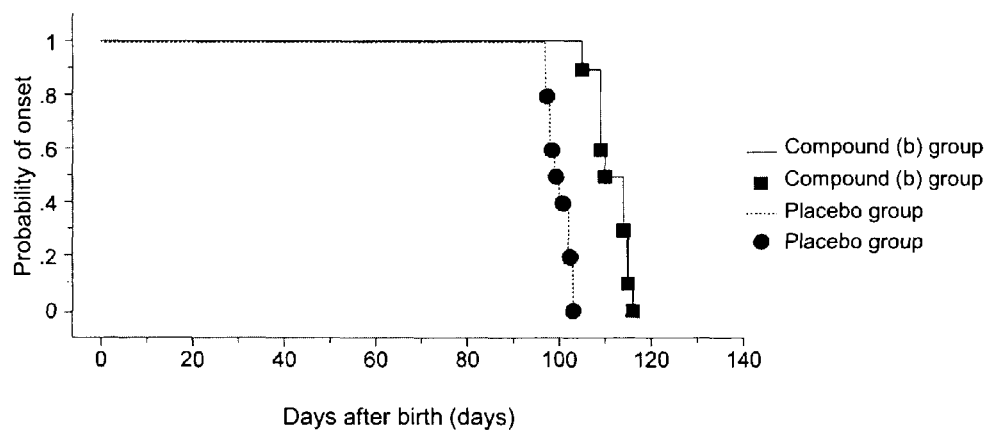
FIG. 11 is a diagram showing the results of a log-rank test of the Kaplan-Meier's method with regard to the day of onset, for the experimental group administered with placebo and the treatment experimental group administered with compound (b) before onset. The vertical axis represents the probability of onset, and the horizontal axis represents days after birth.
Figure 12:
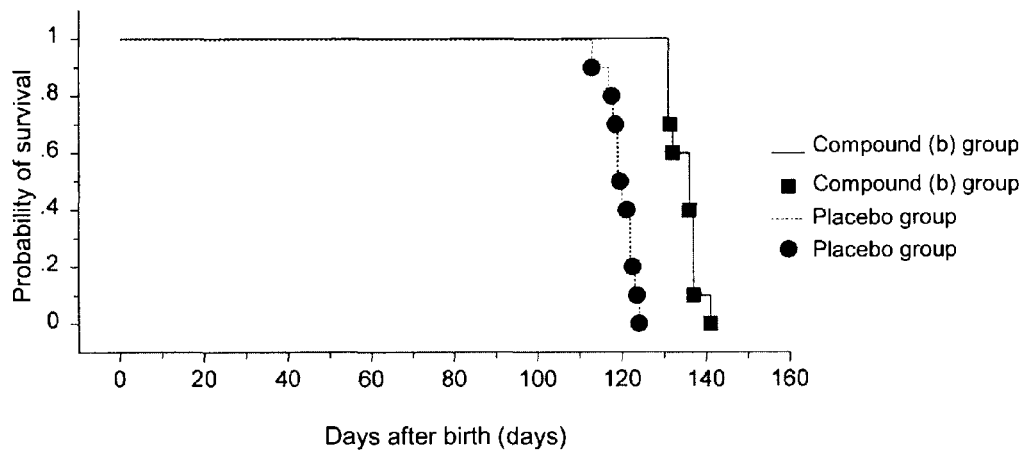
FIG. 12 is a diagram showing the results of a log-rank test of the Kaplan-Meier's method with regard to the survival period, for the experimental group administered with placebo and the treatment experimental group administered with compound (b) before onset. The vertical axis represents the probability of survival, and the horizontal axis represents days after birth.
Figure 13:
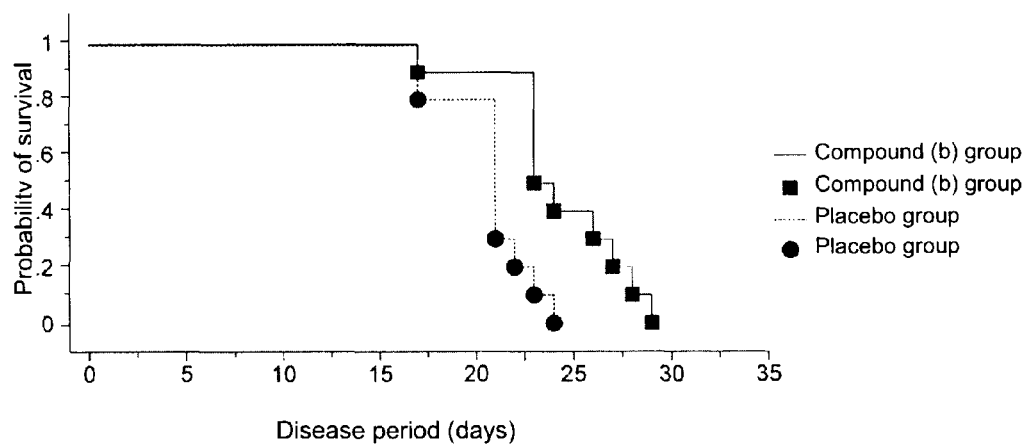
FIG. 13 is a diagram showing the results of a log-rank test of the Kaplan-Meier's method with regard to the disease period, for the experimental group administered with placebo and the treatment experimental group administered with compound (b) before onset. The vertical axis represents the probability of survival, and the horizontal axis represents disease period.
Figure 14:
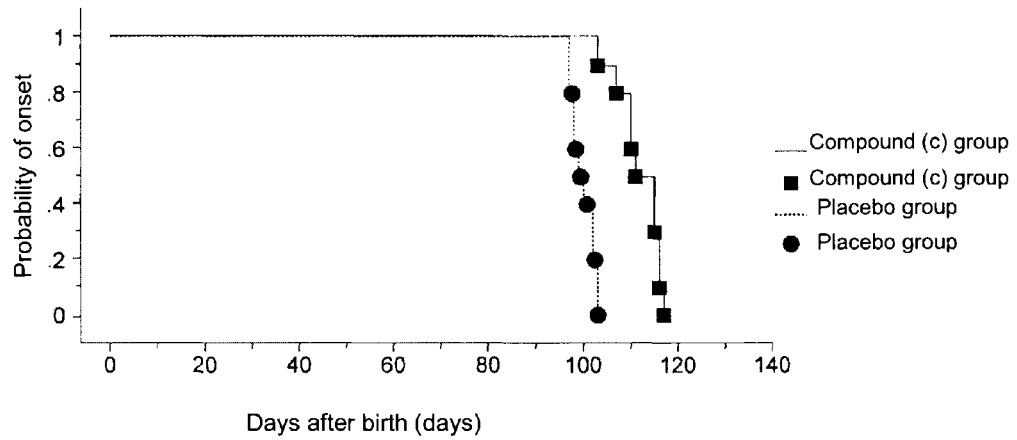
FIG. 14 is a diagram showing the results of a log-rank test of the Kaplan-Meier's method with regard to the day of onset, for the experimental group administered with placebo and the treatment experimental group administered with compound (c) before onset. The vertical axis represents the probability of onset, and the horizontal axis represents days after birth.
Figure 15:
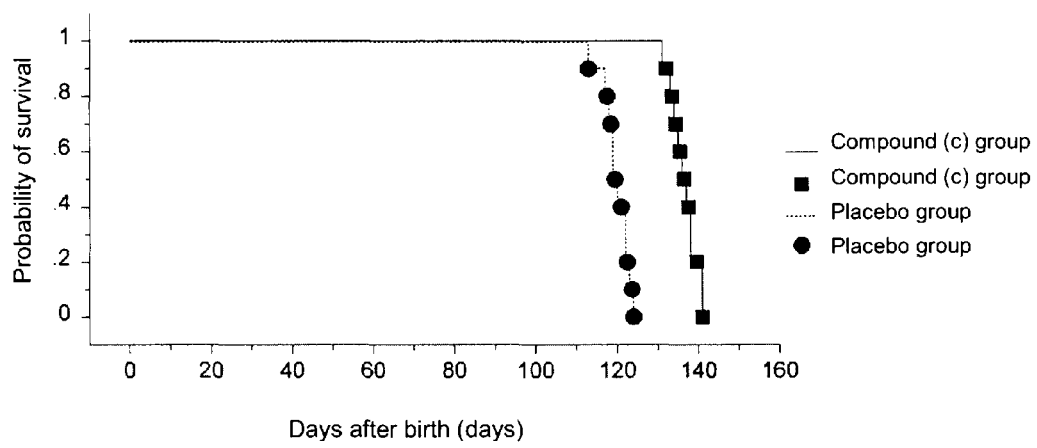
FIG. 15 is a diagram showing the results of a log-rank test of the Kaplan-Meier's method with regard to the survival period, for the experimental group administered with placebo and the treatment experimental group administered with compound (c) before onset. The vertical axis represents the probability of survival, and the horizontal axis represents days after birth.
Figure 16:
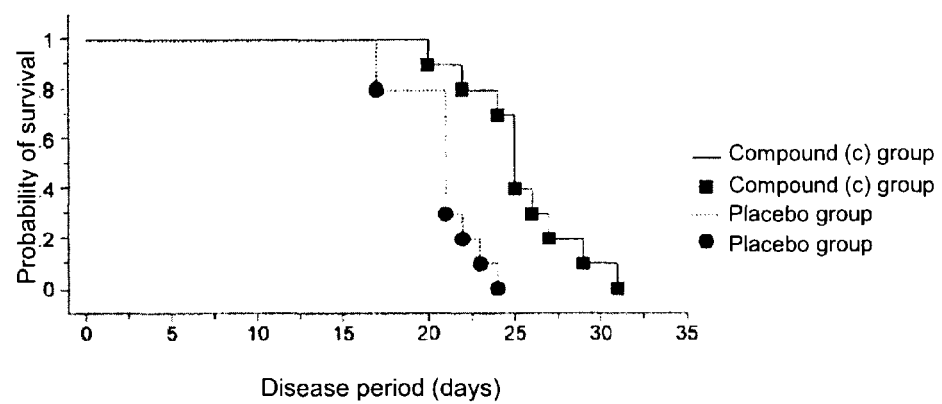
FIG. 16 is a diagram showing the results of a log-rank test of the Kaplan-Meier's method with regard to the disease period, for the experimental group administered with placebo and the treatment experimental group administered with compound (c) before onset. The vertical axis represents the probability of survival, and the horizontal axis represents disease period.

3) Clinical Symptomatological Effectiveness of Administration of Compound (b) Before Onset:

Daily oral administration of 5 mg/kg of compound (b) to G1H-G93A transgenic mice from the $80^{th}$ day after birth resulted in significant delaying of the day of onset (onset delaying effect) ($P<0.001$, Mann-Whitney's U test), significant extension of the survival period (survival period extending effect) ($P<0.001$, Mann-Whitney's U test) and significant extension of the disease period (disease period extending effect) (P<0.01, Mann-Whitney's U test), in comparison to the group administered with placebo (Table 3A). Furthermore, the respective data, i.e., the day of onset (FIG. 11), survival period (FIG. 12) and disease period (FIG. 13) for the group administered with compound (b) before onset, were subjected to a log-rank test of the Kaplan-Meier method to compare with data from the group administered with placebo. As a result, these dates were found to be extended with significant differences. Therefore, it was clearly indicated that the administration of compound (b) before the onset led to the onset delaying effect, survival period extending effect and disease period extending effect. In regard to the time periods for the respective stages of the clinical symptomatological evaluation, the group administered with compound (b) before onset was found to have the extended period of the respective stages with significant difference in comparison to the group administered with placebo: stage 1 (P<0.05, Mann-Whitney's U test); stage 2 (P<0.05, Mann-Whitney's U test); stage 3 (P<0.05, Mann-Whitney's U test); and stage 4 (P<0.05, Mann-Whitney's U test) (Table 3B).

delaying effect) (P<0.001, Mann-Whitney's U test) significant extension of the survival period (survival period extending effect) (P<0.001, Mann-Whitney's U test) and significant extension of the disease period (disease period extending effect) (P<0.01, Mann-Whitney's U test), in comparison to the group administered with placebo (Table 4A). Furthermore, the respective data, i.e., the day of onset (FIG. 14), survival period (FIG. 15) and disease period (FIG. 16) for the group administered with compound (c) before onset, were analyzed using a log-rank test of the Kaplan-Meier method to compare with data from the group administered with placebo. As a result, the date and periods were found to be extended with significant differences. Therefore, it was clearly indicated that the administration of compound (c) before the onset led to the onset delaying effect, survival period extending effect and disease period extending effect. In regard to the time periods for the respective stages of the clinical symptomatological evaluation, the group administered with compound (c) before onset was found to have the extended period

TABLE 3

3A

| | N | Day of onset (days) | Survival period (days) | Disease period (days) |
|---|---|---|---|---|
| Group administered with placebo | 10 | 99.9 ± 2.4 | 119.7 ± 3.3 | 20.8 ± 2.3 |
| | | P* | P* | P** |
| Group administered with compound (b) before onset | 10 | 111.6 ± 3.7 | 134.9 ± 3.4 | 24.4 ± 3.4 |

N: Number of mice used
P* <0.001, Mann-Whitney's U test
P** <0.01, Mann-Whitney's U test

3B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 | 5.4 ± 0.8 | 4.3 ± 0.8 | 2.8 ± 0.6 | 1.7 ± 0.5 |
| | | P* | P* | P* | P* | |
| Group administered with compound (b) before onset | 10 | 7.4 ± 0.7 | 6.4 ± 1.2 | 5.3 ± 1.2 | 3.5 ± 0.5 | 1.7 ± 0.5 |

N: Number of mice used
P* <0.05, Mann-Whitney's U test

4) Clinical Symptomatological Effectiveness of Administration of Compound (c) Before Onset:

Daily oral administration of 5 mg/kg of compound (c) to G1H-G93A transgenic mice from the 80$^{th}$ day after birth resulted in significant delaying of the day of onset (onset of the respective stages with significant difference in comparison to the group administered with placebo: stage 1 (P<0.05, Mann-Whitney's U test); stage 2 (P<0.05, Mann-Whitney's U test); stage 3 (P<0.05, Mann-Whitney's U test); and stage 4 (P<0.05, Mann-Whitney's U test) (Table 4B).

TABLE 4

4A

|  | N | Day of onset (days) | Survival period (days) | Disease period (days) |
|---|---|---|---|---|
| Group administered with placebo | 10 | 99.9 ± 2.4 ⌐<br>      P* | 119.7 ± 3.3 ⌐<br>       P* | 20.8 ± 2.3 ⌐<br>       P** |
| Group administered with compound (c) before onset | 10 | 112.0 ± 4.6 ⌐ | 136.4 ± 3.3 ⌐ | 25.4 ± 3.2 ⌐ |

N: Number of mice used
P* <0.001, Mann-Whitney's U test
P** <0.01, Mann-Whitney's U test

4B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 ⌐<br>      P* | 5.4 ± 0.8 ⌐<br>      P* | 4.3 ± 0.8 ⌐<br>      P* | 2.8 ± 0.6 ⌐<br>      P* | 1.7 ± 0.5 |
| Group administered with compound (c) before onset | 10 | 7.5 ± 0.9 ⌐ | 6.7 ± 1.2 ⌐ | 5.4 ± 1.1 ⌐ | 3.9 ± 1.1 ⌐ | 1.9 ± 0.3 |

N: Number of mice used
P* <0.05, Mann-Whitney's U test

Figure 18:
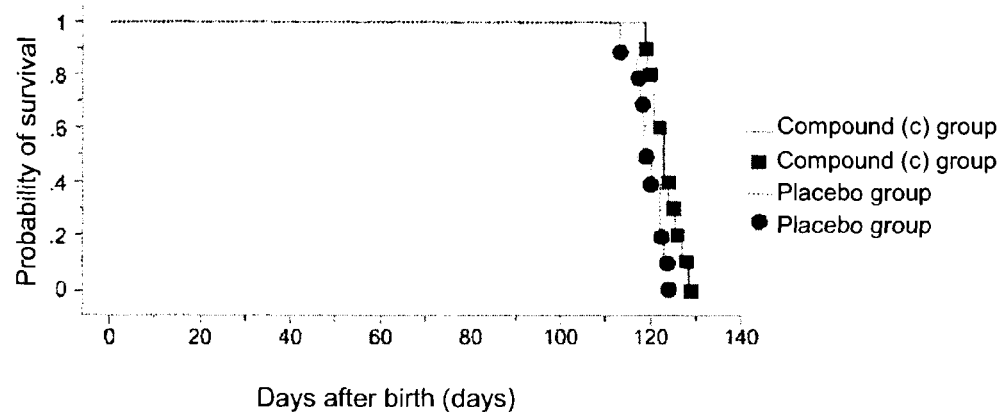
FIG. 18 is a diagram showing the results of a log-rank test of the Kaplan-Meier's method with regard to the survival period, for the experimental group administered with placebo and the treatment experimental group administered with compound (c) after onset. The vertical axis represents the probability of survival, and the horizontal axis represents days after birth.
Figure 19:
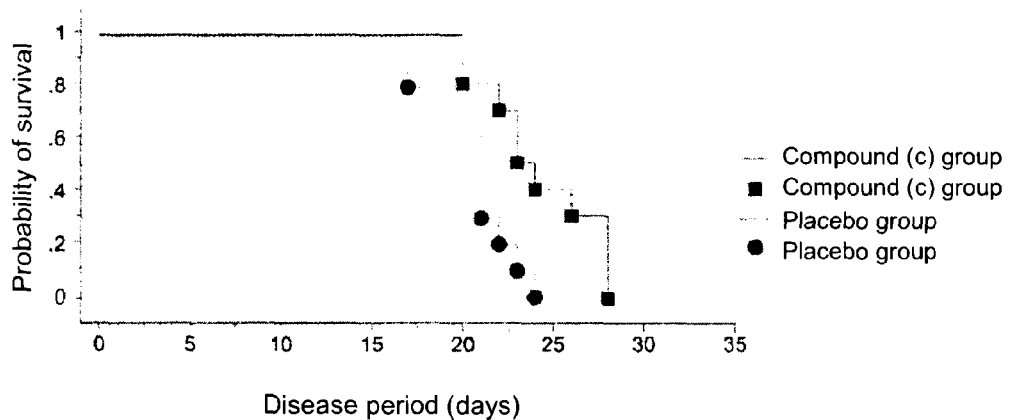
FIG. 19 is a diagram showing the results of a log-rank test of the Kaplan-Meier's method with regard to the disease period, for the experimental group administered with placebo and the treatment experimental group administered with compound (c) after onset. The vertical axis represents the probability of survival, and the horizontal axis represents disease period.

5) Clinical Symptomatological Effectiveness of Administration of Compound (c) after Onset:

Daily oral administration of 5 mg/kg of compound (a) to G1H-G93A transgenic mice from the day of onset resulted in significant extension of the disease period (disease period extending effect) (P<0.05, Mann-Whitney's U test), and therefore, significant extension of the survival period (survival period extending effect) (P<0.05, Mann-Whitney's U test), in comparison to the group administered with placebo (Table 5A). In addition, the two data, i.e., the survival period (FIG. 18) and disease period (FIG. 19) for the group administered with compound (c) after the onset, were analyzed using a log-rank test of the Kaplan-Meier method to compare with data from the group administered with placebo. As a result, these periods were found to be extended with significant differences. Therefore, it was clearly indicated that the administration of compound (c) after the onset led to the survival period extending effect due to the disease period extending effect. In regard to the time periods for the respective stages in the clinical symptomatological evaluation, the group administered with compound (c) after onset was found to have the extended period of stage 3 (P<0.05, Mann-Whitney's U test) and stage 4 (P<0.05, Mann-Whitney's U test) with significant differences in comparison to the group administered with placebo (Table 5B).

TABLE 5

5A

|  | N | Day of onset (days) | Survival period (days) | Disease period (days) |
|---|---|---|---|---|
| Group administered with placebo | 10 | 99.9 ± 2.4 | 119.7 ± 3.3 ⌐<br>       P* | 20.8 ± 2.3 ⌐<br>       P* |
| Group administered with compound (c) before onset | 10 | 100.7 ± 4.3 | 123.9 ± 3.2 ⌐ | 24.2 ± 3.2 ⌐ |

N: Number of mice used
P* <0.05, Mann-Whitney's U test

TABLE 5-continued

5B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 | 5.4 ± 0.8 | 4.3 ± 0.8 ⎤P* | 2.8 ± 0.6 ⎤P* | 1.7 ± 0.5 |
| Group administered with compound (c) before onset | 10 | 7.6 ± 1.2 | 6.2 ± 0.8 | 5.4 ± 1.1 ⎦ | 3.5 ± 0.5 ⎦ | 1.5 ± 0.5 |

N: Number of mice used
P* <0.05, Mann-Whitney's U test

Figure 21:
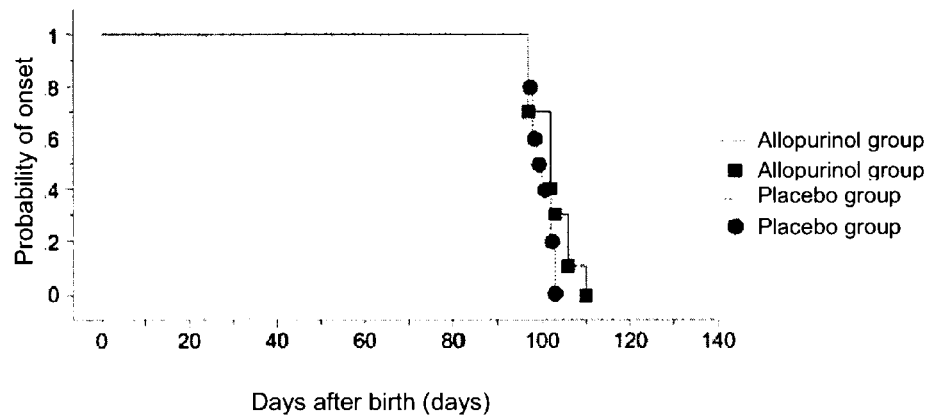
FIG. 21 is a diagram showing the results of a log-rank test of the Kaplan-Meier's method with regard to the probability of onset, for the experimental group administered with placebo and the treatment experimental group administered with allopurinol before onset. The vertical axis represents the probability of onset, and the horizontal axis represents days after birth.
Figure 22:
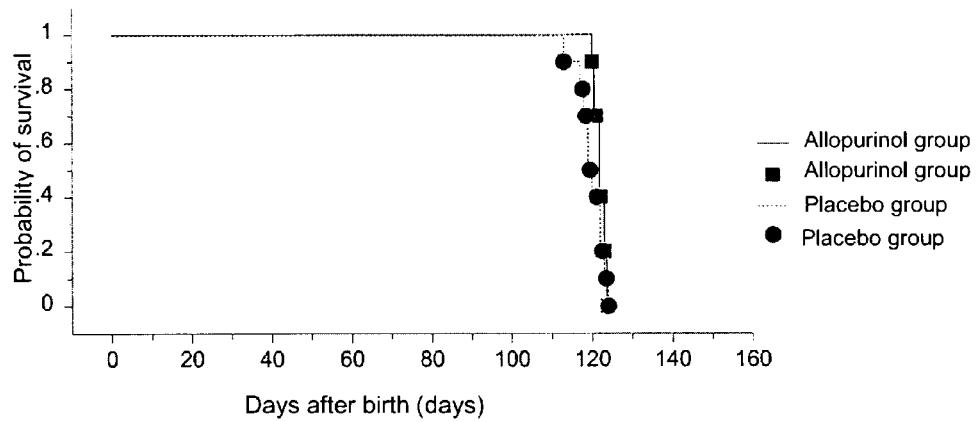
FIG. 22 is a diagram showing the results of a log-rank test of the Kaplan-Meier's method with regard to the probability of survival, for the experimental group administered with placebo and the treatment experimental group administered with allopurinol before onset. The vertical axis represents the probability of survival, and the horizontal axis represents days after birth.
Figure 23:
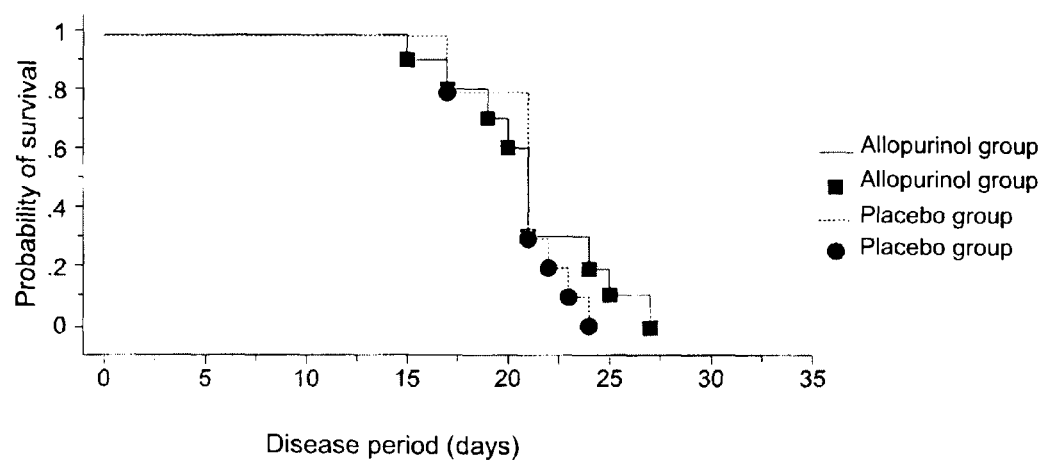
FIG. 23 is a diagram showing the results of a log-rank test of the Kaplan-Meier's method with regard to the disease period, for the experimental group administered with placebo and the treatment experimental group administered with allopurinol before onset. The vertical axis represents the probability of survival, and the horizontal axis represents disease period.

6) Clinical Symptomatological Effectiveness of Administration of Allopurinol Before Onset:

Daily oral administration of 5 mg/kg of allopurinol to G1H-G93A transgenic mice from the 80$^{th}$ day after birth did not result in significant delaying of the day of onset (onset delaying effect) (P>0.05, Mann-Whitney's U test), significant extension of the survival period (survival period extending effect) (P>0.05, Mann-Whitney's U test) or significant extension of the disease period (disease period extending effect) (P>0.05, Mann-Whitney's U test), in comparison to the group administered with placebo (Table 6A). Furthermore, the respective data, i.e., the day of onset (FIG. 21), survival period (FIG. 22) and disease period (FIG. 23) for the group administered with allopurinol, were analyzed using a log-rank test of the Kaplan-Meier method to compare with data from the group administered with placebo. As a result, these data were not found to be extended. Therefore, it was clearly indicated that the administration of allopurinol before the onset did not lead to the onset delaying effect, survival period extending effect or disease period extending effect. In regard to the time periods for the respective stages of the clinical symptomatological evaluation, the group administered with allopurinol before onset was not found to have the extended period of respective stages with significant differences in comparison to the group administered with placebo: stage 1 (P>0.05, Mann-Whitney's U test); stage 2 (P>0.05, Mann-Whitney's U test); stage 3 (P>0.05, Mann-Whitney's U test); stage 4 (P>0.05, Mann-Whitney's U test); and stage 5 (P>0.05, Mann-Whitney's U test) (Table 6B).

TABLE 6

6A

| | N | Day of onset (days) | Survival period (days) | Disease period (days) |
|---|---|---|---|---|
| Group administered with placebo | 10 | 99.9 ± 2.4 ⎤P | 119.7 ± 3.3 ⎤P | 20.8 ± 2.3 ⎤P |
| Group administered allopurinol (a) before onset | 10 | 102.2 ± 4.4 ⎦ | 122.2 ± 1.3 ⎦ | 21.0 ± 3.6 ⎦ |

N: Number of mice used
P* >0.05, Mann-Whitney's U test

6B

| Clinical symptomatic stage | N | Stage 1 (days) | Stage 2 (days) | Stage 3 (days) | Stage 4 (days) | Stage 5 (days) |
|---|---|---|---|---|---|---|
| Group administered with placebo | 10 | 6.6 ± 0.7 ⎤P | 5.4 ± 0.8 ⎤P | 4.3 ± 0.8 ⎤P | 2.8 ± 0.6 ⎤P | 1.7 ± 0.5 ⎤P |
| Group administered with allopurinol before onset | 10 | 6.8 ± 1.1 ⎦ | 5.4 ± 1.3 ⎦ | 4.4 ± 1.2 ⎦ | 2.9 ± 0.7 ⎦ | 1.5 ± 0.5 ⎦ |

N: Number of mice used
P* >0.05, Mann-Whitney's U test

3. Results of Exercise Tolerance Test for Respective Experimental Groups Administered with Placebo or Drugs 1) Experimental Group Administered with Placebo:

In the wild-type mice from the same littermates, which were the normal control group to the experimental group administered with placebo, the scores in the respective exercise tolerance tests (the extension reflex test, inclined plane test, footprint test, rotarod test and beam balance test) were score=0 for all of the 10 animal samples throughout the entire process.

In regard to the evaluation of the respective exercise tolerance tests for the G1H-G93A transgenic mice in the experimental group administered with placebo, the following results were obtained. That is, for the scores of the extension reflex test, score=0.0±0.0 was obtained on the 70$^{th}$ day, 75$^{th}$ day, 80$^{th}$ day, 85$^{th}$ day, 90$^{th}$ day and 95$^{th}$ day after birth; score=0.4±0.5 was obtained on the 100$^{th}$ day; score=1.0±0.0 was obtained on the 105$^{th}$ day; score=1.4±0.5 was obtained on the 110$^{th}$ day; score=1.9±0.3 was obtained on the 115$^{th}$ day; and score=2.0±0.0 was obtained from the 120$^{th}$ day to 140$^{th}$ day (Table 7 to Table 9). For the scores of the inclined plane test, score=0.0±0.0 was obtained on the 70$^{th}$ day, 75$^{th}$ day, 80$^{th}$ day, 85$^{th}$ day, 90$^{th}$ day, 95$^{th}$ day and 100$^{th}$ day after birth; score=0.2±0.4 was obtained on the 105$^{th}$ day; score=1.0±0.8 was obtained on the 110$^{th}$ day; score=2.3±0.5 was obtained on the 115$^{th}$ day; and score=3.0±0.0 was obtained from the 120$^{th}$ day to 140$^{th}$ day (Table 10 to Table 12). For the scores of the footprint test, score=0.0±0.0 was obtained on the 70$^{th}$ day, 75$^{th}$ day, 80$^{th}$ day, 85$^{th}$ day, 90$^{th}$ day and 95$^{th}$ day after birth; score=0.4±0.5 was obtained on the 100$^{th}$ day; score=1.4±0.5 was obtained on the 105$^{th}$ day; score=2.3±0.5 was obtained on the 110$^{th}$ day; score=3.3±0.5 was obtained on the 115$^{th}$ day; and score=4.0±0.0 was obtained from the 120$^{th}$ day to 140$^{th}$ day (Table 13 to Table 15). For the scores of the rotarod test, score=0.0±0.0 was obtained on the 70$^{th}$ day, 75$^{th}$ day, 80$^{th}$ day, 85$^{th}$ day, 90$^{th}$ day and 95$^{th}$ day after birth; score=0.7±0.8 was obtained on the 100$^{th}$ day; score=2.1±0.9 was obtained on the 105$^{th}$ day; and score=3.0±0.0 was obtained from the 110$^{th}$ day to 140$^{th}$ day (Table 16 to Table 18). For the scores of the beam balance test, score=0.0±0.0 was obtained on the 70$^{th}$ day, 75$^{th}$ day, 80$^{th}$ day, 85$^{th}$ day, 90$^{th}$ day and 95$^{th}$ day after birth; score=0.4±0.5 was obtained on the 100$^{th}$ day; score=1.4±0.5 was obtained on the 105$^{th}$ day; and score=2.0±0.0 was obtained from the 110$^{th}$ day to 140$^{th}$ day (Table 19 to Table 21).

2) Treatment Experimental Group Administered with Compound (a) Before Onset:

In regard to the evaluation of the respective exercise tolerance tests for the G1H-G93A transgenic mice in the treatment experimental group administered with compound (a) before onset, the following results were obtained. That is, for the scores of the extension reflex test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.5±0.5 was obtained on the 115$^{th}$ day; score=0.9±0.7 was obtained on the 120$^{th}$ day; score=1.5±0.5 was obtained on the 125$^{th}$ day; score 1.9±0.3 was obtained on the 130$^{th}$ day; and score=2.0±0.0 was obtained on the 135$^{th}$ day and 140$^{th}$ day (Table 7). For the scores of the inclined plane test, score=0.0±0.0 was obtained on the 70$^{th}$ day, 75 day, 80$^{th}$ day, 85$^{th}$ day, 90 day, 95 day, 100$^{th}$ day, 105$^{th}$ day and 110$^{th}$ day after birth; score=0.1±0.3 was obtained on the 115$^{th}$ day; score=0.4±0.5 was obtained on the 120$^{th}$ day; score=1.1±0.9 was obtained on the 125$^{th}$ day; score=2.1±0.9 was obtained on the 130$^{th}$ day; score=2.7±0.5 was obtained on the 135$^{th}$ day; and score=3.0±0.0 was obtained on the 140$^{th}$ day (Table 10). For the scores of the footprint test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.6±0.7 was obtained on the 115$^{th}$ day; score=1.8±0.9 was obtained on the 120$^{th}$ day; score=2.8±0.4 was obtained on the 125$^{th}$ day; score=3.4±0.5 was obtained on the 130$^{th}$ day; score=3.9±0.3 was obtained on the 135$^{th}$ day; and score=4.0±0.0 was obtained on the 140$^{th}$ day (Table 13). For the scores of the rotarod test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.3±0.7 was obtained on the 110$^{th}$ day; score=1.2±1.3 was obtained on the 115$^{th}$ day; score=2.2±0.9 was obtained on the 120$^{th}$ day; score=2.7±0.5 was obtained on the 125$^{th}$ day; and score=3.0±0.0 was obtained from the 130$^{th}$ day to 140$^{th}$ day (Table 16). For the scores of the beam balance test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.7±0.8 was obtained on the 115$^{th}$ day; score=1.2±0.9 was obtained on the 120$^{th}$ day; score=1.7±0.5 was obtained on the 125$^{th}$ day; and score=2.0±0.0 was obtained from the 130$^{th}$ day to 140$^{th}$ day (Table 19).

3) Treatment Experimental Group Administered with Compound (b) Before Onset:

In regard to the evaluation of the respective exercise tolerance tests for the G1H-G93A transgenic mice in the treatment experimental group administered with compound (b) before onset, the following results were obtained. That is, for the scores of the extension reflex test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105 day after birth; score=0.1±0.3 was obtained on the 110$^{th}$ day; score=0.5±0.5 was obtained on the 115$^{th}$ day; score=1.3±0.5 was obtained on the 120$^{th}$ day; score=1.8±0.4 was obtained on the 125$^{th}$ day; and score=2.0±0.0 was obtained from the 130$^{th}$ day to 140$^{th}$ day (Table 8). For the scores of the inclined plane test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day, 105$^{th}$ day and 110$^{th}$ day after birth; score=0.1±0.3 was obtained on the 115$^{th}$ day; score=0.6±0.7 was obtained on the 120$^{th}$ day; score=1.4±0.7 was obtained on the 125$^{th}$ day; score=2.3±0.7 was obtained on the 130$^{th}$ day; score=2.9±0.3 was obtained on the 135$^{th}$ day; and score=3.0±0.0 was obtained on the 140$^{th}$ day (Table 11). For the scores of the footprint test, score=0.0±0.0 was obtained on the 70$^{th}$ day, 75 day, 80 h day, 85$^{th}$ day, 90 day, 95 day, 100$^{th}$ day and 105$^{th}$ day after birth; score=0.1±0.3 was obtained on the 110$^{th}$ day; score=0.6±0.7 was obtained on the 115$^{th}$ day; score=1.8±1.0 was obtained on the 120$^{th}$ day; score=2.8±0.4 was obtained on the 125$^{th}$ day; score=3.4±0.5 was obtained on the 130$^{th}$ day; score=3.9±0.3 was obtained on the 135$^{th}$ day; and score=4.0±0.0 was obtained on the 140$^{th}$ day (Table 14). For the scores of the rotarod test, score=0.0±0.0 was obtained on the 70 day, 75$^{th}$ day, 80$^{th}$ day, 85$^{th}$ day, 90 day, 95 day, 100$^{th}$ day and 105$^{th}$ day after birth; score=0.5±0.7 was obtained on the 110$^{th}$ day; score=1.3±1.1 was obtained on the 115$^{th}$ day; score=2.5±0.5 was obtained on the 120$^{th}$ day; and score=3.0±0.0 was obtained from the 125$^{th}$ day to 140$^{th}$ day (Table 17). For the scores of the beam balance test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.6±0.7 was obtained on the 115$^{th}$ day; score=1.5±0.5 was obtained on the 120$^{th}$ day; and score=2.0±0.0 was obtained from the 125$^{th}$ day to 140$^{th}$ day (Table 20).

4) Treatment Experimental Group Administered with Compound (c) Before Onset:

In regard to the evaluation of the respective exercise tolerance tests for the G1H-G93A transgenic mice in the treatment experimental group administered with compound (c) before onset, the following results were obtained. That is, for the scores of the extension reflex test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.5±0.5 was obtained on the 115$^{th}$ day; score=1.1±0.6 was obtained on the 120$^{th}$ day; score=1.7±0.5 was obtained on the 125$^{th}$ day; and score=2.0±0.0 was obtained from the 130$^{th}$ day to 140$^{th}$ day (Table 9). For the scores of the inclined plane test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day, 105$^{th}$ day and 110$^{th}$ day after birth; score=0.1±0.3 was obtained on the 115$^{th}$ day; score=0.8±0.6 was obtained on the 120$^{th}$ day; score=1.2±0.8 was obtained on the 125$^{th}$ day; score=2.3±0.7 was obtained on the 130$^{th}$ day; score=2.9±0.3 was obtained on the 135$^{th}$ day; and score=3.0±0.0 was obtained on the 140$^{th}$ day (Table 12). For the scores of the footprint test, score=0.0±0.0 was obtained on the 70$^{th}$ day, 75 day, 80 day, 85 day, 90 day, 95$^{th}$ day, 100$^{th}$ day and 105$^{th}$ day after birth; score=0.1±0.3 was obtained on the 110$^{th}$ day; score=0.7±0.8 was obtained on the 115$^{th}$ day; score=1.6±1.0 was obtained on the 120$^{th}$ day; score=2.7±0.5 was obtained on the 125$^{th}$ day; score=3.3±0.5 was obtained on the 130$^{th}$ day; score=3.9±0.3 was obtained on the 135$^{th}$ day; and score=4.0±0.0 was obtained on the 140$^{th}$ day (Table 15). For the scores of the rotarod test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.4±0.8 was obtained on the 110$^{th}$ day; score=1.3±1.3 was obtained on the 115$^{th}$ day; score 2.5±0.5 was obtained on the 120$^{th}$ day; and score=3.0±0.0 was obtained from the 125$^{th}$ day to 140$^{th}$ day (Table 18). For the scores of the beam balance test, score=0.0±0.0 was obtained on the 70$^{th}$ day, 75$^{th}$ day, 80$^{th}$ day, 85$^{th}$ day, 90$^{th}$ day, 95$^{th}$ day, 100$^{th}$ day and 105$^{th}$ day after birth; score=0.1±0.3 was obtained on the 110$^{th}$ day; score=0.7±0.8 was obtained on the 115$^{th}$ day; score=1.4±0.7 was obtained on the 120$^{th}$ day; and score=2.0±0.0 was obtained from the 125$^{th}$ day to 140$^{th}$ day (Table 21).

4. Analysis Results for Exercise Tolerance Test on Effectiveness of Drugs

1) Effectiveness of Treatment by Administration of Compound (a) Before Onset on Exercise Tolerance Tests:

When 5 mg/kg of compound (a) was orally administered to G1H-G93A transgenic mice everyday from the 80$^{th}$ day after birth, significant effects (P<0.005, Mann-Whitney's U test) were shown in the data of the extension reflex test at the 105$^{th}$ day, 110$^{th}$ day, 115$^{th}$ day and 120$^{th}$ day, as compared to the group administered with placebo (Table 7). In regard to the inclined plane test, significant effects (P<0.05, Mann-Whitney's U test) were shown at the 110$^{th}$ day, 115$^{th}$ day, 120$^{th}$ day, 125$^{th}$ day and 130$^{th}$ day, as compared to the group administered with placebo (Table 10). In regard to the footprint test, significant effects (P<0.05, Mann-Whitney's U test) were shown at the 105$^{th}$ day, 110$^{th}$ day, 115$^{th}$ day, 120$^{th}$ day, 125$^{th}$ day and 130$^{th}$ day, as compared to the group administered with placebo (Table 13). In regard to the rotarod test, significant effects (P<0.005, Mann-Whitney's U test) were shown at the 105$^{th}$ day, 110$^{th}$ day and 115$^{th}$ day, as compared to the group administered with placebo (Table 16). In regard to the beam balance test, significant effects (P<0.005, Mann-Whitney's U test) were shown at the 105$^{th}$ day, 110$^{th}$ day and 115$^{th}$ day, as compared to the group administered with placebo (Table 19).

2) Effectiveness of Treatment by Administration of Compound (b) Before Onset on Exercise Tolerance Tests:

When 5 mg/kg of compound (b) was orally administered to G1H-G93A transgenic mice everyday from the 80$^{th}$ day after birth, significant effects (P<0.01, Mann-Whitney's U test) were shown in the data of the extension reflex test at the 105$^{th}$ day, 110$^{th}$ day, 115$^{th}$ day and 120$^{th}$ day, as compared to the group administered with placebo (Table 8). In regard to the inclined plane test, significant effects (P<0.05, Mann-Whitney's U test) were shown at the 110$^{th}$ day, 115$^{th}$ day, 120$^{th}$ day, 125$^{th}$ day and 130$^{th}$ day, as compared to the group administered with placebo (Table 11). In regard to the footprint test, significant effects (P<0.05, Mann-Whitney's U test) were shown at the 105$^{th}$ day, 110$^{th}$ day, 115$^{th}$ day, 120$^{th}$ day, 125$^{th}$ day and 130$^{th}$ day, as compared to the group administered with placebo (Table 14). In regard to the rotarod test, significant effects (P<0.001, Mann-Whitney's U test) were shown at the 105$^{th}$ day, 110$^{th}$ day and 115$^{th}$ day, as compared to the group administered with placebo (Table 17). In regard to the beam balance test, significant effects (P<0.001, Mann-Whitney's U test) were shown at the 105$^{th}$ day, 110$^{th}$ day and 115$^{th}$ day, as compared to the group administered with placebo (Table 20).

3) Effectiveness of Treatment by Administration of Compound (c) Before Onset on Exercise Tolerance Tests:

When 5 mg/kg of compound (c) was orally administered to G1H-G93A transgenic mice everyday from the 80$^{th}$ day after birth, significant effects (P<0.005, Mann-Whitney's U test) were shown in the data of the extension reflex test at the 105$^{th}$ day, 110$^{th}$ day, 115$^{th}$ day and 120$^{th}$ day, as compared to the group administered with placebo (Table 9). In regard to the inclined plane test, significant effects (P<0.05, Mann-Whitney's U test) were shown at the 110$^{th}$ day, 115$^{th}$ day, 120$^{th}$ day, 125$^{th}$ day and 130$^{th}$ day, as compared to the group administered with placebo (Table 12). In regard to the footprint test, significant effects (P<0.01, Mann-Whitney's U test) were shown at the 105$^{th}$ day, 110$^{th}$ day, 115$^{th}$ day, 120$^{th}$ day, 125$^{th}$ day and 130$^{th}$ day, as compared to the group administered with placebo (Table 15). In regard to the rotarod test, significant effects (P<0.005, Mann-Whitney's U test) were shown at the 105$^{th}$ day, 110$^{th}$ day and 115$^{th}$ day, as compared to the group administered with placebo (Table 18). In regard to the beam balance test, significant effects (P<0.005, Mann-Whitney's U test) were shown at the 105$^{th}$ day, 110$^{th}$ day and 115$^{th}$ day, as compared to the group administered with placebo (Table 21).

TABLE 7

Extension reflex test

| Number of days after birth | Group administered with placebo | Group administered with compound (a) before onset | Mann-Whitney's U test | |
|---|---|---|---|---|
| 70$^{th}$ day after birth | 0.0 ± 0.0 | 0.0 ± 0.0 | p > 0.9 | |
| 75$^{th}$ day after birth | 0.0 ± 0.0 | 0.0 ± 0.0 | p > 0.9 | |
| 80$^{th}$ day after birth | 0.0 ± 0.0 | 0.0 ± 0.0 | p > 0.9 | |
| 85$^{th}$ day after birth | 0.0 ± 0.0 | 0.0 ± 0.0 | p > 0.9 | |
| 90$^{th}$ day after birth | 0.0 ± 0.0 | 0.0 ± 0.0 | p > 0.9 | |
| 95$^{th}$ day after birth | 0.0 ± 0.0 | 0.0 ± 0.0 | p > 0.9 | |
| 100$^{th}$ day after birth | 0.4 ± 0.5 | 0.0 ± 0.0 | P = 0.13 | |
| 105$^{th}$ day after birth | 1.0 ± 0.0 | 0.0 ± 0.0 | P = 0.0002 | <0.0005 |
| 110$^{th}$ day after birth | 1.4 ± 0.5 | 0.1 ± 0.3 | P = 0.0004 | <0.0005 |
| 115$^{th}$ day after birth | 1.9 ± 0.3 | 0.5 ± 0.5 | P = 0.0003 | <0.0005 |
| 120$^{th}$ day after birth | 2.0 ± 0.0 | 0.9 ± 0.7 | P = 0.0025 | <0.005 |
| 125$^{th}$ day after birth | 2.0 ± 0.0 | 1.5 ± 0.5 | P = 0.0588 | |
| 130$^{th}$ day after birth | 2.0 ± 0.0 | 1.9 ± 0.3 | p > 0.9 | |
| 135$^{th}$ day after birth | 2.0 ± 0.0 | 2.0 ± 0.0 | p > 0.9 | |
| 140$^{th}$ day after birth | 2.0 ± 0.0 | 2.0 ± 0.0 | p > 0.9 | |

TABLE 8

Extension reflex test

| Number of days after birth | Group administered with placebo | Group administered with compound (b) before onset | Mann-Whitney's U test | |
|---|---|---|---|---|
| 70th day after birth | 0.0 ± 0.0 | 0.0 ± 0.0 | p > 0.99 | |
| 75th day after birth | 0.0 ± 0.0 | 0.0 ± 0.0 | p > 0.99 | |
| 80th day after birth | 0.0 ± 0.0 | 0.0 ± 0.0 | p > 0.99 | |
| 85th day after birth | 0.0 ± 0.0 | 0.0 ± 0.0 | p > 0.99 | |
| 90th day after birth | 0.0 ± 0.0 | 0.0 ± 0.0 | p > 0.99 | |
| 95th day after birth | 0.0 ± 0.0 | 0.0 ± 0.0 | p > 0.99 | |
| 100th day after birth | 0.4 ± 0.5 | 0.0 ± 0.0 | P = 0.13 | |
| 105th day after birth | 1.0 ± 0.0 | 0.0 ± 0.0 | P = 0.0002 | <0.0005 |
| 110th day after birth | 1.4 ± 0.5 | 0.1 ± 0.3 | P = 0.0004 | <0.0005 |
| 115th day after birth | 1.9 ± 0.3 | 0.5 ± 0.5 | P = 0.0003 | <0.0005 |
| 120th day after birth | 2.0 ± 0.0 | 1.3 ± 0.5 | P = 0.008 | <0.01 |
| 125th day after birth | 2.0 ± 0.0 | 1.8 ± 0.4 | P = 0.44 | |
| 130th day after birth | 2.0 ± 0.0 | 2.0 ± 0.0 | p > 0.99 | |
| 135th day after birth | 2.0 ± 0.0 | 2.0 ± 0.0 | p > 0.99 | |
| 140th day after birth | 2.0 ± 0.0 | 2.0 ± 0.0 | p > 0.99 | |

TABLE 9

Extension reflex test

| Number of days after birth | Group administered with placebo | Group administered with compound (c) before onset | Mann-Whitney's U test | |
|---|---|---|---|---|
| 70th day after birth | 0.0 ± 0.0 | 0.0 ± 0.0 | p > 0.99 | |
| 75th day after birth | 0.0 ± 0.0 | 0.0 ± 0.0 | p > 0.99 | |
| 80th day after birth | 0.0 ± 0.0 | 0.0 ± 0.0 | p > 0.99 | |
| 85th day after birth | 0.0 ± 0.0 | 0.0 ± 0.0 | p > 0.99 | |
| 90th day after birth | 0.0 ± 0.0 | 0.0 ± 0.0 | p > 0.99 | |
| 95th day after birth | 0.0 ± 0.0 | 0.0 ± 0.0 | p > 0.99 | |
| 100th day after birth | 0.4 ± 0.5 | 0.0 ± 0.0 | P = 0.13 | |
| 105th day after birth | 1.0 ± 0.0 | 0.0 ± 0.0 | P = 0.0002 | <0.0005 |
| 110th day after birth | 1.4 ± 0.5 | 0.1 ± 0.3 | P = 0.0004 | <0.0005 |
| 115th day after birth | 1.9 ± 0.3 | 0.5 ± 0.5 | P = 0.0003 | <0.0005 |
| 120th day after birth | 2.0 ± 0.0 | 1.1 ± 0.6 | P = 0.0025 | <0.005 |
| 125th day after birth | 2.0 ± 0.0 | 1.7 ± 0.5 | P = 0.25 | |
| 130th day after birth | 2.0 ± 0.0 | 2.0 ± 0.0 | p > 0.99 | |
| 135th day after birth | 2.0 ± 0.0 | 2.0 ± 0.0 | p > 0.99 | |
| 140th day after birth | 2.0 ± 0.0 | 2.0 ± 0.0 | p > 0.99 | |

TABLE 10

Inclined plane test

| Number of days after birth | Group administered with placebo | Group administered with compound (a) before onset | Mann-Whitney's U test | |
|---|---|---|---|---|
| 70th day after birth | 0.0 ± 0.0 | 0.0 ± 0.0 | p > 0.99 | |
| 75th day after birth | 0.0 ± 0.0 | 0.0 ± 0.0 | p > 0.99 | |
| 80th day after birth | 0.0 ± 0.0 | 0.0 ± 0.0 | p > 0.99 | |
| 85th day after birth | 0.0 ± 0.0 | 0.0 ± 0.0 | p > 0.99 | |
| 90th day after birth | 0.0 ± 0.0 | 0.0 ± 0.0 | p > 0.99 | |
| 95th day after birth | 0.0 ± 0.0 | 0.0 ± 0.0 | p > 0.99 | |
| 100th day after birth | 0.0 ± 0.0 | 0.0 ± 0.0 | p > 0.99 | |
| 105th day after birth | 0.2 ± 0.4 | 0.0 ± 0.0 | P = 0.44 | |
| 110th day after birth | 1.0 ± 0.8 | 0.0 ± 0.0 | P = 0.0082 | <0.01 |
| 115th day after birth | 2.3 ± 0.5 | 0.1 ± 0.3 | P = 0.0002 | <0.0005 |
| 120th day after birth | 3.0 ± 0.0 | 0.4 ± 0.5 | P = 0.0002 | <0.0005 |
| 125th day after birth | 3.0 ± 0.0 | 1.1 ± 0.9 | P = 0.0002 | <0.0005 |
| 130th day after birth | 3.0 ± 0.0 | 2.1 ± 0.9 | p = 0.023 | <0.05 |
| 135th day after birth | 3.0 ± 0.0 | 2.7 ± 0.5 | P = 0.25 | |
| 140th day after birth | 3.0 ± 0.0 | 3.0 ± 0.0 | p > 0.99 | |

TABLE 11

Inclined plane test

| Number of days after birth | Group administered with placebo | Group administered with compound (b) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.0 ± 0.0 | 0.0 ± 0.0 | P = 0.13 | |
| 105th day after birth | 0.2 ± 0.4 | 0.0 ± 0.0 | P = 0.449 | |
| 110th day after birth | 1.0 ± 0.8 | 0.0 ± 0.0 | P = 0.0082 | <0.01 |
| 115th day after birth | 2.3 ± 0.5 | 0.1 ± 0.3 | P = 0.0002 | <0.0005 |
| 120th day after birth | 3.0 ± 0.0 | 0.6 ± 0.7 | P = 0.0002 | <0.0005 |
| 125th day after birth | 3.0 ± 0.0 | 1.4 ± 0.7 | P = 0.0002 | <0.0005 |
| 130th day after birth | 3.0 ± 0.0 | 2.3 ± 0.7 | P = 0.023 | <0.05 |
| 135th day after birth | 3.0 ± 0.0 | 2.9 ± 0.3 | P = 0.705 | |
| 140th day after birth | 3.0 ± 0.0 | 3.0 ± 0.0 | P > 0.99 | |

TABLE 12

Inclined plane test

| Number of days after birth | Group administered with placebo | Group administered with compound (c) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.0 ± 0.0 | 0.0 ± 0.0 | P = 0.13 | |
| 105th day after birth | 0.2 ± 0.4 | 0.0 ± 0.0 | P = 0.449 | |
| 110th day after birth | 1.0 ± 0.8 | 0.0 ± 0.0 | P = 0.0082 | <0.01 |
| 115th day after birth | 2.3 ± 0.5 | 0.1 ± 0.3 | P = 0.0002 | <0.0005 |
| 120th day after birth | 3.0 ± 0.0 | 0.8 ± 0.6 | P = 0.0002 | <0.0005 |
| 125th day after birth | 3.0 ± 0.0 | 1.2 ± 0.8 | P = 0.0002 | <0.0005 |
| 130th day after birth | 3.0 ± 0.0 | 2.3 ± 0.7 | P = 0.023 | <0.05 |
| 135th day after birth | 3.0 ± 0.0 | 2.9 ± 0.3 | P = 0.705 | |
| 140th day after birth | 3.0 ± 0.0 | 3.0 ± 0.0 | P > 0.99 | |

TABLE 13

Footprint test

| Number of days after birth | Group administered with placebo | Group administered with compound (a) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.3 ± 0.5 | 0.1 ± 0.3 | P = 0.0002 | <0.0005 |
| 115th day after birth | 3.3 ± 0.5 | 0.6 ± 0.7 | P = 0.0002 | <0.0005 |
| 120th day after birth | 4.0 ± 0.0 | 1.8 ± 0.9 | P = 0.0002 | <0.0005 |
| 125th day after birth | 4.0 ± 0.0 | 2.8 ± 0.4 | P = 0.0002 | <0.0005 |
| 130th day after birth | 4.0 ± 0.0 | 3.4 ± 0.5 | P = 0.0233 | <0.05 |
| 135th day after birth | 4.0 ± 0.0 | 3.9 ± 0.3 | P = 0.256 | |
| 140th day after birth | 4.0 ± 0.0 | 4.0 ± 0.0 | P > 0.99 | |

TABLE 14

Footprint test

| Number of days after birth | Group administered with placebo | Group administered with compound (b) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.3 ± 0.5 | 0.1 ± 0.3 | P = 0.0002 | <0.0005 |
| 115th day after birth | 3.3 ± 0.5 | 0.6 ± 0.7 | P = 0.0002 | <0.0005 |
| 120th day after birth | 4.0 ± 0.0 | 1.8 ± 1.0 | P = 0.0002 | <0.0005 |
| 125th day after birth | 4.0 ± 0.0 | 2.8 ± 0.4 | P = 0.0002 | <0.0005 |
| 130th day after birth | 4.0 ± 0.0 | 3.4 ± 0.5 | P = 0.0233 | <0.05 |
| 135th day after birth | 4.0 ± 0.0 | 3.9 ± 0.3 | P = 0.7055 | |
| 140th day after birth | 4.0 ± 0.0 | 4.0 ± 0.0 | P > 0.99 | |

TABLE 15

Footprint test

| Number of days after birth | Group administered with placebo | Group administered with compound (c) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.3 ± 0.5 | 0.1 ± 0.3 | P = 0.0002 | <0.0005 |
| 115th day after birth | 3.3 ± 0.5 | 0.7 ± 0.8 | P = 0.0002 | <0.0005 |
| 120th day after birth | 4.0 ± 0.0 | 1.6 ± 1.0 | P = 0.0002 | <0.0005 |
| 125th day after birth | 4.0 ± 0.0 | 2.7 ± 0.5 | P = 0.0002 | <0.0005 |
| 130th day after birth | 4.0 ± 0.0 | 3.3 ± 0.5 | P = 0.0082 | <0.01 |
| 135th day after birth | 4.0 ± 0.0 | 3.9 ± 0.3 | P = 0.7055 | |
| 140th day after birth | 4.0 ± 0.0 | 4.0 ± 0.0 | P > 0.99 | |

TABLE 16

Rotarod test

| Number of days after birth | Group administered with placebo | Group administered with compound (a) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.7 ± 0.8 | 0.0 ± 0.0 | P = 0.0588 | |
| 105th day after birth | 2.1 ± 0.9 | 0.0 ± 0.0 | P = 0.0002 | <0.0005 |
| 110th day after birth | 3.0 ± 0.0 | 0.3 ± 0.7 | P = 0.0002 | <0.0005 |
| 115th day after birth | 3.0 ± 0.0 | 1.2 ± 1.3 | P = 0.0025 | <0.005 |
| 120th day after birth | 3.0 ± 0.0 | 2.2 ± 0.9 | P = 0.0588 | |
| 125th day after birth | 3.0 ± 0.0 | 2.7 ± 0.5 | P = 0.2568 | |
| 130th day after birth | 3.0 ± 0.0 | 3.0 ± 0.0 | P > 0.99 | |
| 135th day after birth | 3.0 ± 0.0 | 3.0 ± 0.0 | P > 0.99 | |
| 140th day after birth | 3.0 ± 0.0 | 3.0 ± 0.0 | P > 0.99 | |

TABLE 17

Rotarod test

| Number of days after birth | Group administered with placebo | Group administered with compound (b) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.7 ± 0.8 | 0.0 ± 0.0 | P = 0.0588 | |
| 105th day after birth | 2.1 ± 0.9 | 0.0 ± 0.0 | P = 0.0002 | <0.0005 |
| 110th day after birth | 3.0 ± 0.0 | 0.5 ± 0.7 | P = 0.0002 | <0.0005 |
| 115th day after birth | 3.0 ± 0.0 | 1.3 ± 1.1 | P = 0.0007 | <0.001 |
| 120th day after birth | 3.0 ± 0.0 | 2.5 ± 0.5 | P = 0.0588 | |
| 125th day after birth | 3.0 ± 0.0 | 3.0 ± 0.0 | P > 0.99 | |
| 130th day after birth | 3.0 ± 0.0 | 3.0 ± 0.0 | P > 0.99 | |
| 135th day after birth | 3.0 ± 0.0 | 3.0 ± 0.0 | P > 0.99 | |
| 140th day after birth | 3.0 ± 0.0 | 3.0 ± 0.0 | P > 0.99 | |

TABLE 18

Rotarod test

| Number of days after birth | Group administered with placebo | Group administered with compound (c) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.7 ± 0.8 | 0.0 ± 0.0 | P = 0.0588 | |
| 105th day after birth | 2.1 ± 0.9 | 0.0 ± 0.0 | P = 0.0002 | <0.0005 |
| 110th day after birth | 3.0 ± 0.0 | 0.4 ± 0.8 | P = 0.0002 | <0.0005 |
| 115th day after birth | 3.0 ± 0.0 | 1.3 ± 1.3 | P = 0.0025 | <0.005 |
| 120th day after birth | 3.0 ± 0.0 | 2.5 ± 0.5 | P = 0.0588 | |
| 125th day after birth | 3.0 ± 0.0 | 3.0 ± 0.0 | P > 0.99 | |
| 130th day after birth | 3.0 ± 0.0 | 3.0 ± 0.0 | P > 0.99 | |
| 135th day after birth | 3.0 ± 0.0 | 3.0 ± 0.0 | P > 0.99 | |
| 140th day after birth | 3.0 ± 0.0 | 3.0 ± 0.0 | P > 0.99 | |

TABLE 19

Beam balance test

| Number of days after birth | Group administered with placebo | Group administered with compound (a) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.0 ± 0.0 | 0.1 ± 0.3 | P = 0.0002 | <0.0005 |
| 115th day after birth | 2.0 ± 0.0 | 0.7 ± 0.8 | P = 0.0025 | <0.005 |
| 120th day after birth | 2.0 ± 0.0 | 1.2 ± 0.9 | P = 0.0588 | |
| 125th day after birth | 2.0 ± 0.0 | 1.7 ± 0.5 | P = 0.2568 | |
| 130th day after birth | 2.0 ± 0.0 | 2.0 ± 0.0 | P > 0.99 | |
| 135th day after birth | 2.0 ± 0.0 | 2.0 ± 0.0 | P > 0.99 | |
| 140th day after birth | 2.0 ± 0.0 | 2.0 ± 0.0 | | |

TABLE 20

Beam balance test

| Number of days after birth | Group administered with placebo | Group administered with compound (b) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.0 ± 0.0 | 0.1 ± 0.3 | P = 0.0002 | <0.0005 |
| 115th day after birth | 2.0 ± 0.0 | 0.6 ± 0.7 | P = 0.0007 | <0.001 |
| 120th day after birth | 2.0 ± 0.0 | 1.5 ± 0.5 | P = 0.0588 | |
| 125th day after birth | 2.0 ± 0.0 | 2.0 ± 0.0 | P > 0.99 | |
| 130th day after birth | 2.0 ± 0.0 | 2.0 ± 0.0 | P > 0.99 | |
| 135th day after birth | 2.0 ± 0.0 | 2.0 ± 0.0 | P > 0.99 | |
| 140th day after birth | 2.0 ± 0.0 | 2.0 ± 0.0 | P > 0.99 | |

TABLE 21

Beam balance test

| Number of days after birth | Group administered with placebo | Group administered with compound (c) before onset | Mann-Whitney's U test | |
|---|---|---|---|---|
| 70th day after birth | 0.0 ± 0.0 | 0.0 ± 0.0 | P > 0.99 | |
| 75th day after birth | 0.0 ± 0.0 | 0.0 ± 0.0 | P > 0.99 | |
| 80th day after birth | 0.0 ± 0.0 | 0.0 ± 0.0 | P > 0.99 | |
| 85th day after birth | 0.0 ± 0.0 | 0.0 ± 0.0 | P > 0.99 | |
| 90th day after birth | 0.0 ± 0.0 | 0.0 ± 0.0 | P > 0.99 | |
| 95th day after birth | 0.0 ± 0.0 | 0.0 ± 0.0 | P > 0.99 | |
| 100th day after birth | 0.4 ± 0.5 | 0.0 ± 0.0 | P = 0.13 | |
| 105th day after birth | 1.4 ± 0.5 | 0.0 ± 0.0 | P = 0.0002 | <0.0005 |
| 110th day after birth | 2.0 ± 0.0 | 0.1 ± 0.3 | P = 0.0002 | <0.0005 |
| 115th day after birth | 2.0 ± 0.0 | 0.7 ± 0.8 | P = 0.0025 | <0.005 |
| 120th day after birth | 2.0 ± 0.0 | 1.4 ± 0.7 | P = 0.0588 | |
| 125th day after birth | 2.0 ± 0.0 | 2.0 ± 0.0 | P > 0.99 | |
| 130th day after birth | 2.0 ± 0.0 | 2.0 ± 0.0 | P > 0.99 | |
| 135th day after birth | 2.0 ± 0.0 | 2.0 ± 0.0 | P > 0.99 | |
| 140th day after birth | 2.0 ± 0.0 | 2.0 ± 0.0 | P > 0.99 | |

5. Results of Histopathological Investigation for Respective Experimental Groups Administered with Placebo or Drugs 1) Experimental Group Administered with Placebo:

For the G1H-G93A transgenic mice of the experimental group administered with placebo, it was found that the number of spinal cord anterior horn cells in the cervical segment=4.3±3.5, the number of spinal cord anterior horn cells in the thoracic segment=2.5±4.3, and the number of spinal cord anterior horn cells in the lumbar segment=3.7±2.4 (Tables 22, 23, 24 and 25).

2) Treatment Experimental Group Administered with Compound (a) Before Onset:

For the G1H-G93A transgenic mice of the treatment experimental group administered with compound (a) before onset, it was found that the number of spinal cord anterior horn cells in the cervical segment=3.3±3.1, the number of spinal cord anterior horn cells in the thoracic segment=1.6±2.1, and the number of spinal cord anterior horn cells in the lumbar segment=3.7±3.3 (Table 22).

3) Treatment Experimental Group Administered with Compound (a) after Onset:

For the G1H-G93A transgenic mice of the treatment experimental group administered with compound (a) after onset, it was found that the number of spinal cord anterior horn cells in the cervical segment=4.8±3.7, the number of spinal cord anterior horn cells in the thoracic segment=2.3±2.2, and the number of spinal cord anterior horn cells in the lumbar segment=4.1±4.4 (Table 23).

4) Treatment Experimental Group Administered with Compound (b) Before Onset:

For the G1H-G93A transgenic mice of the treatment experimental group administered with compound (b) before onset, it was found that the number of spinal cord anterior horn cells in the cervical segment=4.6±2.0, the number of spinal cord anterior horn cells in the thoracic segment=1.9±1.7, and the number of spinal cord anterior horn cells in the lumbar segment=5.3±2.7 (Table 24).

5) Treatment Experimental Group Administered with Compound (c) Before Onset:

For the G1H-G93A transgenic mice of the treatment experimental group administered with compound (c) before onset, it was found that the number of spinal cord anterior horn cells in the cervical segment=5.2±4.3, the number of spinal cord anterior horn cells in the thoracic segment=1.6±1.7, and the number of spinal cord anterior horn cells in the lumbar segment=4.1±3.8 (Table 25).

6. Results of Histopathological Analysis after Treatment by Administration of Drugs 1) Results of Histopathological Analysis after Treatment by Administration of Compound (a) Before Onset:

Between the treatment experimental group in which G1H-G93A transgenic mice were orally administered with 5 mg/kg of compound (a) everyday from the 80th day after birth and the experimental group administered with placebo, no significant difference was histopathologically observed (P>0.05, Mann-Whitney's U test) in the number of spinal cord anterior horn cells in the cervical segment of the spinal cord, thoracic segment or lumbar segment at the end stage (Table 22).

2) Results of Histopathological Analysis According to Treatment by Administration of Compound (a) after Onset:

Between the treatment experimental group in which G1H-G93A transgenic mice were orally administered with 5 mg/kg of compound (a) everyday from the day of onset and the experimental group administered with placebo, no significant difference was histopathologically observed (P>0.05, Mann-Whitney's U test) in the number of spinal cord anterior horn cells in the cervical segment of the spinal cord, thoracic segment or lumbar segment at the end stage (Table 23).

3) Results of Histopathological Analysis According to Treatment by Administration of Compound (b) Before Onset:

Between the treatment experimental group in which G1H-G93A transgenic mice were orally administered with 5 mg/kg of compound (b) everyday from the 80$^{th}$ day after birth and the experimental group administered with placebo, no significant difference was histopathologically observed (P>0.05, Mann-Whitney's U test) in the number of spinal cord anterior horn cells in the cervical segment of the spinal cord, thoracic segment or lumbar segment at the end stage (Table 24).

4) Results of Histopathological Analysis According to Treatment by Administration of Compound (c) Before Onset:

Between the treatment experimental group in which G1H-G93A transgenic mice were orally administered with 5 mg/kg of compound (c) everyday from the 80$^{th}$ day after birth and the experimental group administered with placebo, no significant difference was histopathologically observed (P>0.05, Mann-Whitney's U test) in the number of spinal cord anterior horn cells in the cervical segment of the spinal cord, thoracic segment or lumbar segment at the end stage (Table 25).

TABLE 22

| | | Results of histopathological analysis | | |
|---|---|---|---|---|
| | N | Number of cervical spinal cord anterior horn cells | Number of thoracic spinal cord anterior horn cells | Number of lumbar spinal cord anterior horn cells |
| Group administered with placebo | 10 | 4.3 ± 3.5 ⎤ P | 2.5 ± 4.3 ⎤ P | 3.7 ± 2.4 ⎤ P |
| Group administered with compound (a) before onset | 10 | 3.3 ± 3.1 ⎦ | 1.6 ± 2.1 ⎦ | 3.7 ± 3.3 ⎦ |

N: Number of mice used
P >0.05, Mann-Whitney's U test

TABLE 23

| | | Results of histopathological analysis | | |
|---|---|---|---|---|
| | N | Number of cervical spinal cord anterior horn cells | Number of thoracic spinal cord anterior horn cells | Number of lumbar spinal cord anterior horn cells |
| Group administered with placebo | 10 | 4.3 ± 3.5 ⎤ P | 2.5 ± 4.3 ⎤ P | 3.7 ± 2.4 ⎤ P |
| Group administered with compound (a) before onset | 10 | 4.8 ± 3.7 ⎦ | 2.3 ± 2.2 ⎦ | 4.1 ± 4.4 ⎦ |

N: Number of mice used
P >0.05, Mann-Whitney's U test

TABLE 24

| | | Results of histopathological analysis | | |
|---|---|---|---|---|
| | N | Number of cervical spinal cord anterior horn cells | Number of thoracic spinal cord anterior horn cells | Number of lumbar spinal cord anterior horn cells |
| Group administered with placebo | 10 | 4.3 ± 3.5 ⎤ P | 2.5 ± 4.3 ⎤ P | 3.7 ± 2.4 ⎤ P |
| Group administered with compound (b) before onset | 10 | 4.6 ± 2.0 ⎦ | 1.9 ± 1.7 ⎦ | 5.3 ± 2.7 ⎦ |

N: Number of mice used
P >0.05, Mann-Whitney's U test

TABLE 25

| | | Results of histopathological analysis | | |
|---|---|---|---|---|
| | N | Number of cervical spinal cord anterior horn cells | Number of thoracic spinal cord anterior horn cells | Number of lumbar spinal cord anterior horn cells |
| Group administered with placebo | 10 | 4.3 ± 3.5 ⎤ P | 2.5 ± 4.3 ⎤ P | 3.7 ± 2.4 ⎤ P |
| Group administered with compound (c) before onset | 10 | 5.2 ± 4.3 ⎦ | 1.6 ± 1.7 ⎦ | 4.1 ± 3.8 ⎦ |

N: Number of mice used
P >0.05, Mann-Whitney's U test

The invention claimed is:

1. A method for treating amyotrophic lateral sclerosis, wherein the method comprises administering to a subject in need thereof, an effective amount of a compound represented by the following formula (1), (2) or (3), or a salt thereof:

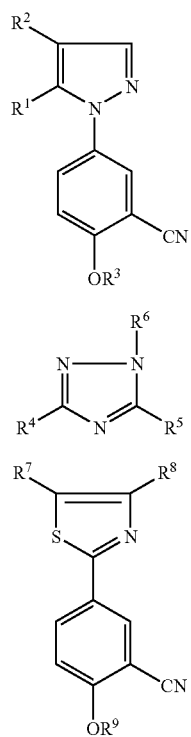

wherein $R^1$ represents a hydrogen atom, a halogen atom or an amino group;

$R^2$ represents a carboxyl group or a $C_{1-4}$ alkoxycarbonyl group;

$R^3$ represents a $C_{4-6}$ alkyl group, a $C_{3-6}$ cycloalkyl group or a $C_{3-6}$ cycloalkyl-$C_{1-4}$ alkyl group, all of which are optionally substituted with one to two substituents selected from halogen, hydroxyl, $C_{1-4}$ alkoxy, carboxy, $C_{1-4}$ alkoxycarbonyl and acyloxy;

$R^4$ represents a pyridyl group which is optionally substituted with one to two substituents selected from halogen, cyano and phenyl; or a phenyl group which is optionally substituted with one to two substituents selected from cyano, nitro, $C_{1-4}$ alkoxy, N—$C_{1-4}$ alkylpiperazino, $C_{1-4}$ alkylthio, phenylthio and $C_{1-4}$ alkylamino;

$R^5$ represents a pyridyl group which is optionally substituted with a substituent selected from cyano, $C_{1-4}$ alkyl, halogen, $C_{1-4}$ alkoxy and $C_{1-4}$ alkylthio;

$R^6$ represents a hydrogen atom, or a pivaloyloxy-$C_{1-4}$ alkyl group;

$R^7$ represents a carboxyl group, a $C_{1-6}$ alkoxycarbonyl group, a carbamoyl group, or a mono- or di-$C_{1-6}$ alkylaminocarbonyl group;

$R^8$ represents a hydrogen atom, a $C_{1-6}$ alkyl group or a phenyl group; and $R^9$ represents a hydrogen atom or a $C_{1-10}$ alkyl group.

2. The method according to claim 1, wherein:

in the formula (1), $R^1$ is a hydrogen atom, a halogen atom or an amino group; $R^2$ is a carboxyl group or a $C_{1-4}$ alkoxycarbonyl group; and $R^3$ is a $C_{4-6}$ alkyl group, a $C_{3-6}$ cycloalkyl group or a $C_{3-6}$ cycloalkyl-$C_{1-4}$ alkyl group;

in the formula (2), $R^4$ is a pyridyl group having one or two substituents selected from cyano, and halogen; $R^5$ is a pyridyl group which is optionally substituted with one or two substituents selected from cyano, halogen, $C_{1-4}$ alkoxy and $C_{1-4}$ alkylthio; and $R^6$ is a hydrogen atom; and in the formula (3), $R^7$ is a carboxyl group or a $C_{1-6}$ alkoxycarbonyl group;

$R^8$ is a hydrogen atom or a $C_{1-6}$ alkyl group; and $R^9$ is a $C_{1-8}$ alkyl group.

3. The method according to claim 1, wherein in the formula (1), $R^1$ is a hydrogen atom, $R^2$ is a carboxyl group, and $R^3$ is a $C_{4-6}$ alkyl group; in the formula (2), $R^4$ is a cyanopyridyl group, $R^5$ is a pyridyl group, and $R^6$ is a hydrogen atom; and in the formula (3), $R^7$ is a carboxyl group, $R^8$ is a $C_{1-6}$ alkyl group, and $R^9$ is a $C_{2-6}$ alkyl group.

4. The method according to claim 1, wherein $R^1$ is a hydrogen atom, $R^2$ is a carboxyl group, and $R^3$ is a neopentyl group; in the formula (2), $R^4$ is a 2-cyanopyridin-4-yl group, $R^5$ is a pyridin-4-yl group, and $R^6$ is a hydrogen atom; and in the formula (3), $R^7$ is a carboxyl group, $R^8$ is a methyl group, and $R^9$ is an isobutyl group.

5. The method according to claim 1, comprising administering the compound of formula (1) and wherein $R^1$ is a hydrogen atom, a halogen atom or an amino group; $R^2$ is a carboxyl group or a $C_{1-4}$ alkoxycarbonyl group; and $R^3$ is a $C_{4-6}$ alkyl group, a $C_{3-6}$ cycloalkyl group or a $C_{3-6}$ cycloalkyl-$C_{1-4}$ alkyl group.

6. The method according to claim 1, comprising administering the compound of formula (2) and wherein $R^4$ is a pyridyl group having one or two substituents selected from cyano, and halogen; $R^5$ is a pyridyl group which is optionally substituted with one or two substituents selected from cyano, halogen, $C_{1-4}$ alkoxy and $C_{1-4}$ alkylthio; and $R^6$ is a hydrogen atom.

7. The method according to claim 1, comprising administering the compound of formula (3) and wherein $R^7$ is a carboxyl group or a $C_{1-6}$ alkoxycarbonyl group;

$R^8$ is a hydrogen atom or a $C_{1-6}$ alkyl group; and $R^9$ is a $C_{1-8}$ alkyl group.

8. The method according to claim 1, comprising administering the compound of formula (1) and wherein $R^1$ is a hydrogen atom, $R^2$ is a carboxyl group, and $R^3$ is a neopentyl group.

9. The method according to claim 1, comprising administering the compound of formula (2) and wherein $R^4$ is a 2-cyanopyridin-4-yl group, $R^5$ is a pyridin-4-yl group, and $R^6$ is a hydrogen atom.

10. The method according to claim 1, comprising administering the compound of formula (3) and wherein $R^7$ is a carboxyl group, $R^8$ is a methyl group, and $R^9$ is an isobutyl group.

11. The method according to claim 1, comprising administering the compound of formula (1) and wherein $R^1$ is a hydrogen atom, $R^2$ is a carboxyl group, and $R^3$ is a $C_{4-6}$ alkyl group.

12. The method according to claim 1, comprising administering the compound of formula (2) and wherein $R^4$ is a cyanopyridyl group, $R^5$ is a pyridyl group, and $R^6$ is a hydrogen atom.

13. The method according to claim 1, comprising administering the compound of formula (3) and wherein $R^7$ is a carboxyl group, $R^8$ is a $C_{1-6}$ alkyl group, and $R^9$ is a $C_{2-6}$ alkyl group.

* * * * *